(12) United States Patent
Shamay

(10) Patent No.: US 10,561,487 B2
(45) Date of Patent: Feb. 18, 2020

(54) METHOD SYSTEM AND FASTENER FOR ANCHORING A CORPUS

(71) Applicant: AMNIS THERAPEUTICS LTD., Or Akiva (IL)

(72) Inventor: Noam Shamay, Beit Uziel (IL)

(73) Assignee: MAJIPA MED LTD., Tel Aviv-Jaffa (IL)

( * ) Notice: Subject to any disclaimer, the term of this patent is extended or adjusted under 35 U.S.C. 154(b) by 248 days.

(21) Appl. No.: 15/671,664

(22) Filed: Aug. 8, 2017

(65) Prior Publication Data

US 2017/0360546 A1 Dec. 21, 2017

Related U.S. Application Data

(60) Division of application No. 14/249,163, filed on Apr. 9, 2014, now Pat. No. 9,833,306, which is a
(Continued)

(30) Foreign Application Priority Data

Oct. 10, 2011 (IL) .......................... 215655

(51) Int. Cl.
*A61F 2/01* (2006.01)
*A61B 17/064* (2006.01)
(Continued)

(52) U.S. Cl.
CPC .............. *A61F 2/01* (2013.01); *A61B 17/064* (2013.01); *A61B 17/221* (2013.01);
(Continued)

(58) Field of Classification Search
CPC ........ A61B 17/221; A61B 2017/22034; A61B 2017/2217; A61B 17/22031; A61B 17/320725; A61F 2002/016
(Continued)

(56) References Cited

U.S. PATENT DOCUMENTS 5,632,754 A * 5/1997 Farley ................ A61B 17/3207
604/22
7,766,921 B2 8/2010 Sepetka et al.
(Continued)

OTHER PUBLICATIONS

I.Q. Grunwald, et al.: "Endovascular Stroke Treatment Today", American Journal of Neuroradiology, vol. 32(2), Feb. 2011, pp. 238-243 (in English).
(Continued)

*Primary Examiner* — Katherine M Shi
(74) *Attorney, Agent, or Firm* — Browdy and Neimark, P.L.L.C.

(57) ABSTRACT

There is described a method, a system, and a device for the anchoring of and into a corpus disposed distally in a conduit by engaging a stranded tube with the corpus and unwinding the wound threads of the stranded tube into unwound threads. Engagement includes the use of handling and manipulation shaft to dispose the stranded tube proximally, distally, or in the interior to the corpus. Unwinding, of the stranded tube is achieved by rotating a tube tool against the stranded tube. Unwinding liberates the helically coiled unwound strands in "corkscrew" rotation into the corpus. Proximal retrieval of a corpus is achieved by proximal retrieval of the stranded tube anchoring the corpus. An unwound stranded tube is operable as a fastener, as an electrical lead, and as a support for a device.

10 Claims, 20 Drawing Sheets

Related U.S. Application Data continuation of application No. PCT/IL2012/000355, filed on Oct. 10, 2012.

(51) Int. Cl.
| | |
|---|---|
| *A61B 17/221* | (2006.01) |
| *A61B 90/00* | (2016.01) |
| *A61B 17/22* | (2006.01) |
| *A61B 17/00* | (2006.01) |

(52) U.S. Cl.
CPC ............ *A61B 2017/00893* (2013.01); *A61B 2017/0641* (2013.01); *A61B 2017/0647* (2013.01); *A61B 2017/2215* (2013.01); *A61B 2017/2217* (2013.01); *A61B 2017/22034* (2013.01); *A61B 2090/08021* (2016.02); *A61F 2002/016* (2013.01)

(58) Field of Classification Search
USPC ........................................ 606/127, 159, 200
See application file for complete search history.

(56) References Cited

U.S. PATENT DOCUMENTS

| | | | |
|---|---|---|---|
| 2005/0033347 A1* | 2/2005 | Rauker | ............... A61F 2/013 |
| | | | 606/200 |
| 2007/0118165 A1 | 5/2007 | Demello et al. | |
| 2007/0260266 A1 | 11/2007 | Karpiel | |
| 2008/0188885 A1 | 8/2008 | Sepetka et al. | |
| 2010/0023035 A1 | 1/2010 | Kontos | |
| 2011/0034863 A1 | 2/2011 | Hoffa | |
| 2011/0213403 A1* | 9/2011 | Aboytes | ............... A61F 2/013 |
| | | | 606/194 |

OTHER PUBLICATIONS

International Search Report (ISR) dated Jan. 23, 2013 (in English) issued in International Application No. PCT/IL2012/000355.
International Preliminary Report on Patentability (IPRP) dated Apr. 15, 2014 (in English) issued in International Application No. PCT/IL2012/000355.

* cited by examiner

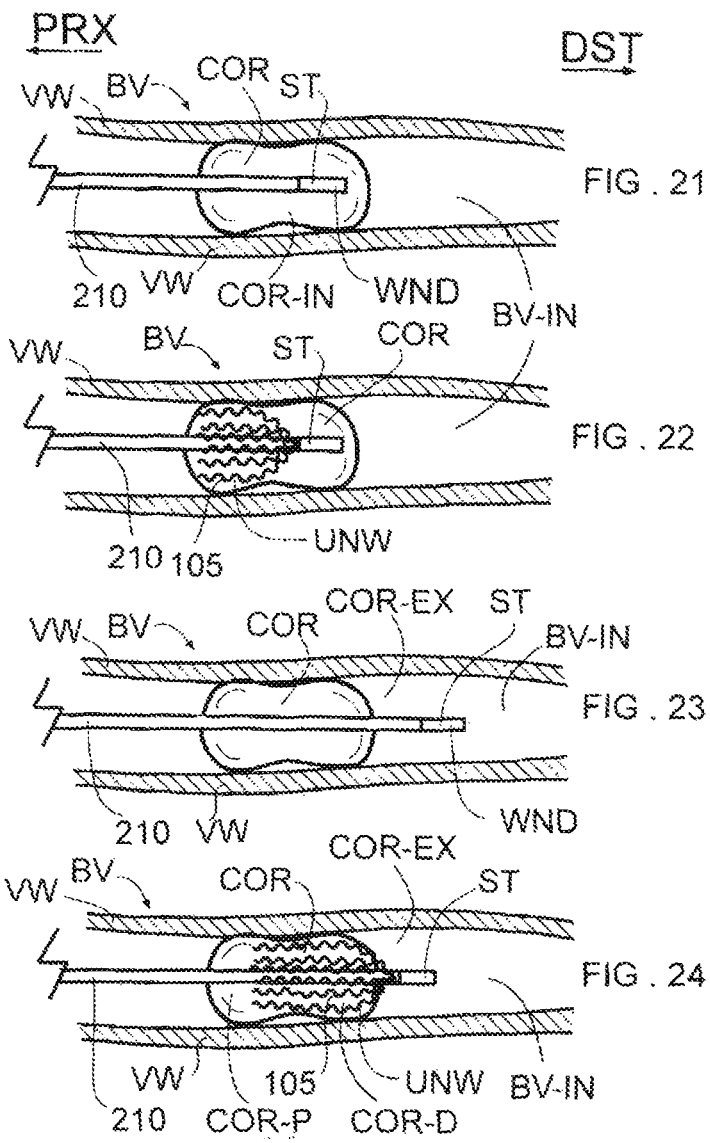

PRX ↑
← ST
← ST-D
← 110
← TT
DST ↓

← ST
← TT

Fig. 43
PRX ↑
← ST
← TT
← 105
← ST
← TT
← 105
DST ↓
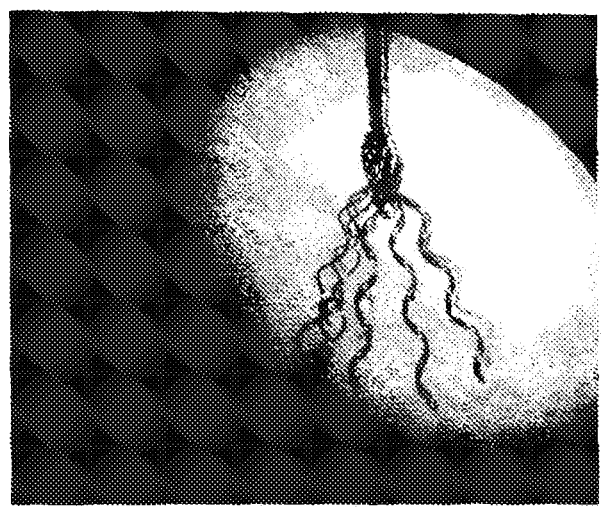
Fig. 44

METHOD SYSTEM AND FASTENER FOR ANCHORING A CORPUS

TECHNICAL FIELD

The embodiments of the method and system described hereinbelow relate to the field of fastening of a body in a conduit, and in particular, to the anchoring of and into a corpus disposed distally in a narrow conduit for corpus retrieval and/or fastening purposes.

BACKGROUND ART

The removal of clots by use of minimally invasive procedures is nowadays a well-established practice. Many patents are known in the field of clot removal and several devices are presently available on the market. The purpose of such devices is to retrieve blood clots without or with only minimal distal embolization or clot fragmentation.

Out of the methods available to remove clots by minimally invasive operation, a common method is the removal of the clot by aspiration. One problem with the aspiration devices is the need for a large lumen to create a sufficient aspiration force for the suction of a thrombus. Another problem is the need of a rigid material to form the tip of the aspiration catheter to withstand strong vacuum forces without collapsing the lumen. To overcome such structural requirements, a relatively sturdy device of rather hefty construction and quite large dimensions is required, which large dimensions prevent aspiration catheters from reaching clots located in narrow vessels such as found in the brain.

Means for retrieving obstructions from a blood vessel are disclosed in U.S. Pat. No. 7,766,921 to I. Sepetka et al., reciting means that are deployed in a collapsed condition and are then expanded within the body.

A study of the presently available means for removing obstructions from a blood vessel, referred to hereinbelow as the study, may be found in "Endovascular Stroke Treatment Today", by I. Q. Grunwald et al. in AJNR, the American Journal of Neuroradiology, Vol. 32, pp. 238-243 of February 2011, www.ajnr.org. The purpose of the study was to review current treatment options in acute ischemic stroke, focusing on the latest advances in the field and devices of mechanical recanalization. These mechanical recanalization devices recently made available for endovascular intracranial thrombectomy show great potential in acute stroke treatments.

Technical Problem

The problem to be solved is how to prevent a major intervention, such as a surgical intervention for example, when in need to penetrate, capture, anchor and retrieve or fasten a penetrable physical body disposed in a conduit. The problem is aggravated when the physical body to be operated upon is disposed distally away and the conduit is of miniature dimensions. Such a physical body may include objects able to cause a total or a partial obstruction of a conduit wherethrough a fluid has to pass. An obstruction may be a body or an object such as a plug or a sponge, but also cellular tissue, a growth, a clot, or a body having a physical volume, and may include penetrable medical implements such as a graft stents, all referred to hereinbelow as a corpus.

Examples of anchoring of and into a penetrable physical body may include, but are not limited to the engagement of an object or of tissue for removal out of a system of ducts, out of a vasculature, or out of an anatomy, which removal techniques are referred to in more details hereinbelow. The problem of retrieving a physical body out of a conduit is presented first. Additional problems such as anchoring for joining together of tissue or anchoring for fastening in place of implements, of grafts, and of physical bodies and the introduction of preparation(s) or medication into tissue are also described hereinbelow.

A conduit may be rigid or flexible and may relate to a pipe, a tube, a blood vessel, or a duct wherein fluid or a substance which may be brought to flow like a fluid may pass-through when the conduit is not obstructed.

One problem to be solved is thus how to retrieve an obstruction such as penetrable tissue disposed distally in a conduit, hence to retrieve a penetrable physical object, i.e. a body of substance, referred to hereinbelow as a corpus, out of a conduit, out of a portion of the anatomy, or out of the vasculature of a body for example. The solution to the problem has to respond to multiple needs and requirements.

One requirement is for a retrieval tool or system able to retrieve a distal corpus by anchoring the proximal side end of the corpus. The problem to be solved is to avoid the necessity of having to pass through the corpus from the proximal side end to the distal side end thereof, and further distally away, to safely anchor, thus catch the corpus before starting proximal retrieval.

Another requirement calls for the realization of a corpus retrieval system of miniaturized dimensions having the ability to pass through a conduit or through blood vessels of small size, such as found deep in the cerebral vasculature.

A further imperative need is to prevent fragmentation of the corpus during an attempt of proximal retrieval, to prevent release of fragments into the fluid flowing in a conduit, or into the blood stream of a blood vessel.

Solution to Problem

The solution is provided by use of a flexible stranded tube formed out of a plurality of prestressed helically coiled threads wound together and forming an interior lumen. In other words, a stranded tube is a hollow coil body made out of a plurality of thread elements to form a piece of flexible wire tubing having a central axis hollow portion. A thread is accepted to be a filament, such as for example, a metallic wire, or a non-metallic thread. A stranded tube may be a helicoidal tube or sleeve wound from a plurality of metallic or non-metallic threads tightly coiled and pressed together in gapless mutual contact with each other. The threads of the stranded tube are preferably disposed as a single layer of threads forming the circumference of the stranded tube. The geometrical shape of the cross-section of the threads may be selected as desired, preferably out of commercially available shapes, but other cross-section shapes are feasible. For example, the cross-section of a thread may be selected to be of circular, square, rectangular, trapezoidal, oval, or of other cross-sectional shape, even though not shown as such in the Figs. The cross-section of the stranded tube is not necessarily circular but may be selected as desired or as available. For example, the cross-section of the stranded tube may be rectangular or oval. For the sake of simplicity, the description hereinbelow refers to and depicts the stranded tube as a cylindrical tube.

One example of a stranded tube is a commercially available product known under the name of Helical Hollow Strand, which is a Trademark, having an open center working channel/lumen, made as a tube with one layer of filars. The stranded tube is also known as a wire stranded hollow prestressed and tightly wound coil body with a multitude of coil elements, made to form flexible tubing having a central axis hollow portion.

The stranded tube may be selected as a flexible tube made of metal such as stainless steel, or Nitinol, or made from non-metallic material, such as a polymer, composite fibers, or another suitable material or of a combination thereof. The stranded tube may be covered or coated with a product such as a friction-reducing coat or layer of solid lubricant for enhancing smooth operation, such as Teflon for example, which is a registered Trademark. A stranded tube is different from a braided tube. In the description hereinbelow, winding is understood in the sense of coiling helically. Furthermore, a coil is accepted as being a ring or a circle when the stranded tube is of circular cross-section, and coiling means refer to the means for forming a thread into a ring or a circle. The direction of winding of the stranded tube may be chosen to be clockwise or anti-clockwise.

FIG. 1 shows an exemplary stranded tube ST commercially available on the market, such as for example from Fort Wayne Metals, USA. Details may be found at www.fwmetals.com. The stranded tube is a basic element of the embodiments of the present invention.

The threads 102 of the stranded tube ST are helically coiled and tightly wound together to form a solid but flexible slender structure, having a pitch distance 103 and a stranded tube lumen 104. The stranded tube ST has an exterior diameter D, an interior diameter d, and a stranded tube longitudinal axis X. A stranded tube ST wound out as few as two wound threads 102 still retains superior push-pull and torque transmission capability relative to a helicoidal spring structure with one thread, such as a helicoidal spring for example. This means that an angular torque and angle of rotation applied at a proximal portion end ST-P of the stranded tube ST are received at the distal portion end ST-D thereof substantially without losses, with the same torque and angle of rotation.

FIG. 2 schematically depicts an example of a stranded tube ST having a stranded tube proximal portion end ST-P oriented toward a proximal direction PRX, and a stranded tube distal portion end ST-D pointing in a distal direction DST. The stranded tube distal portion end ST-D is shown in the unwound state UNW, thus having unwound strands 105 that retain a helically coiled shape after unwinding.

In FIG. 2, the unwound threads 105 at the distal portion end ST-D are shown longitudinally extended and mutually separated apart from each other, in contrast with their mutual tight gapless wound helical coiling state WND forming proximal portion end ST-P of the stranded tube ST. However, each single wound coiled thread 102 separated or liberated, or unwound from the wound stranded tube ST retains the shape of an individual helically coiled unwound thread 105 having a coil pitch and directed along a respective unwound thread longitudinal axis x. The unwound helically threads 105 may expand radially and longitudinally away from the stranded tube longitudinal axis X and may form an angle α therewith. The angle opened between the stranded tube longitudinal axis X and the respective longitudinal axis x of the helically coiled unwound threads 105 is indicated as the angle α. The magnitude of the angle α is controllable but may be positive, thus diverging, negative, hence converging, and also be zero, or parallel to the stranded tube longitudinal axis X.

An individual helically coiled unwound thread 105, or unwound thread 105 for short, is similar in shape to a corkscrew that typically has a high-pitch thread, or coil pitch. The liberated unwound threads 105 may expand somewhat radially relative to the longitudinal axis X of the stranded tube ST. In the longitudinally extended and radially liberated unwound state UNW, the distal ends 108 of the unwound threads 105 may fan out and expand to a diameter larger than the exterior diameter D of the stranded tube ST.

FIG. 3 schematically illustrates the distal liberation from the wound state WND of the threads 102 at the tube distal portion end ST-D into the unwound state UNW of the mutually separated and unwound threads 105 at the distal portion end ST-D of the stranded tube ST. A tube tool TT may be operated to unwind either the proximal portion end ST-P, not shown, or the distal end portion ST-D of the stranded tube ST, as shown in FIG. 3. In FIG. 3, the tube tool TT is disposed in abutment with the distal end portion ST-D and in partial penetration within the lumen 104 of the stranded tube ST, and in co-alignment with the stranded tube longitudinal axis X. However, more than a portion, and possibly the entirety of the tube tool TT may penetrate into the lumen 104 of the stranded tube. In FIG. 3 only four separated unwound threads 105 are shown to keep the drawing simple.

For unwinding thereof, the stranded tube ST may abut the tube tool TT in longitudinal force application through relative rotation about the stranded tube longitudinal axis X. Relative rotation in the winding direction of the stranded tube ST for unwinding thereof means that the stranded tube may be rotated against a tube tool TT which is at standstill, or that the tube tool TT may be rotated respectively to a stationary stranded tube tool, or that both the stranded tube and the tube tool may rotate in opposite direction to create a relative rotation in the winding direction of the stranded tube ST. FIG. 3 shows the abutment of the distal end portion ST-D with the tube tool TT, where rotation in the winding direction of the stranded tube ST is indicated by an arrow marked R. As a result, the tube tool TT that is disposed at the distal end portion ST-D of the stranded tube ST may be operated to unwind and distally liberate wound threads 102 into unwound threads 105, which expand distally and may expand radially.

It is by rotation of the proximal end portion ST-P of the stranded tube ST in the winding direction R of the stranded tube that the unwound threads 105 also rotate in the winding direction R along a respective unwound thread longitudinal axis x, in the same winding direction R. In operation, the tube tool TT may be regarded as if "extruding" the wound threads 102 into distally extending unwound threads 105. At least one, or more, or each one of the unwound helically coiled threads 105, or unwound threads 105 for short, may actually operate for the anchoring of and into the corpus COR as an individual corkscrew appropriate to seize and capture the corpus.

It is by rotational corkscrew-like translation and rotation that the unwound threads 105 may strongly anchor and penetrate into the corpus COR which has to be retrieved proximally out of a distal disposition of a conduit. The skeleton-like, or web-like shape formed by the fanned-out unwound threads 105 that anchor the corpus COR provides structural reinforcement and are causal for the prevention of fragmentation of the corpus.

It is thus possible to take advantage of a stranded tube ST having a plurality of tightly wound coiled threads 102 to retrieve a corpus COR, which is disposed distally in a conduit BV, such as a blood vessel for example. The stranded tube ST has to be appropriately engaged with and relative to the corpus COR and it then suffices to unwind the wound threads 102 and push the unwound threads 105 for their anchoring of and into the corpus. Once at least one unwound coiled thread 105 is anchored, the corpus COR may be removed by help of proximal retrieval of the stranded tube ST to which the corpus is anchored.

Engagement of the wound stranded tube ST with the corpus COR, before unwinding, may include disposing the stranded tube in a disposition proximal to the corpus COR, or in a disposition distal to the corpus, or a in a disposition interior to the corpus. Engaging may also mean disposing the stranded tube in a disposition in proximity of the corpus COR, in abutment with the corpus, and interior to the corpus.

In operation, the stranded tube ST may be rotated about the stranded tube longitudinal axis X for unwinding at least one, a plurality of, or each one wound coiled thread 102 out of the plurality of wound coiled threads along a respective unwound thread longitudinal axis x. Thereby, rotating the stranded tube ST rotates each one unwound coiled thread 105 about the respective unwound thread longitudinal axis x.

Unwinding of a stranded tube ST causing an unwound coiled thread 105 to rotate in corkscrew-fashion about its own longitudinal axis x may not be an easily and intuitively understandable process, but is nevertheless a fact. FIGS. 41 to 44 show pictures illustrating various stages of the unwinding process.

Described hereinbelow are some embodiments using the principle of unwinding wound threads 102 into separate unwound threads 105 that are configured for the anchoring of and into at least one corpus COR for distal retrieval thereof, or for other purposes such as for fastening, connecting and attachment.

In the description hereinbelow, distal refers to the direction of the corpus COR, while proximal is regarded as being the direction of the operator, not shown, thus away from the corpus. Directional terms appearing throughout the specification and claims, e.g. "distal", "proximal", etc., and derivatives thereof, are used for illustrative purposes only, to indicate directions and are not intended to limit the scope of the appended claims. In addition, parts and portions of the embodiments when described herein in detail or not, are described as in their respective orientation relative to the corpus COR. In the specification and claims, each one of the verbs, "comprise" "include" and "have", and conjugates thereof, are used to indicate that the object or objects of the verb are not necessarily a complete listing of members, components, elements or parts of the subject or subjects of the verb.

Advantageous Effects of Invention

One solution described hereinabove provides a method and a system for the use of a stranded tube ST for the anchoring of and into at least one corpus COR, for retrieving the corpus. Each at least one unwound thread 105 inserted into the corpus COR is configured to operate as a corkscrew for the solid anchoring of and into the corpus. The method and the system are configured for operation is narrow distal conduits BV.

Furthermore, an unwound stranded tube ST may be used as a fastener for fixedly attaching the stranded tube to at least one corpus and/or to and with implement(s).

Commercially available stranded tubes ST may have dimensions as small as an exterior diameter D of 0.1 mm, with threads 102 having a strand diameter d of 0.01 mm, and are available in length of some 1.5 to 2 meters.

SUMMARY

It is an object of the present invention to provide a method, a system, and a device for anchoring of and into at least one corpus COR disposed in a conduit BV, including operating a stranded tube ST having a plurality of wound coiled threads 102. The method, system, and device may comprise engaging the stranded tube with the at least one corpus, unwinding at least one wound thread out of the plurality of wound threads, and anchoring the at least one unwound thread 105 into the at least one corpus.

It is another object of the present invention to provide a tube tool TT, engaging the tube tool with the stranded tube ST, and operating the tube tool for unwinding the stranded tube.

It is yet an object of the present invention to provide the disposition of the stranded tube in a disposition proximal to the corpus, a disposition distal to the corpus, and a disposition interior to the corpus. Engaging the stranded tube with the corpus may further include disposing the stranded tube in a disposition in proximity of the corpus, a disposition in abutment with the corpus, and a disposition interior to the corpus.

It is still an object of the present invention to provide a way for retrieving the anchored corpus proximally by proximally retrieving the stranded tube and for preventing fragmentation of the corpus by adding thereto structural reinforcement.

It is yet still an object of the present invention to provide for the operation of the at least one anchored unwound threads as a fastener, which may be anchored alone and in combination into a corpus and/or a conduit, and/or an implement. It is further possible to coat one or more threads of the stranded tube with a product.

It is yet still one object of the present invention to provide for an unwound thread alone and in combination as an electrode and as an electrical lead.

It is yet still one more object of the present invention to provide for the rotation of the stranded tube relative to the tube tool about a longitudinal axis of the stranded tube, and for the rotation and the orientation of each unwound thread along a respective unwound thread longitudinal axis. Orientation of unwound threads includes disposing the longitudinal axis of the unwound thread at an angle relative to the longitudinal axis of the stranded tube, and control of that angle.

It is yet still one further object of the present invention to provide the unwound threads of the stranded tube with a direction of winding, and to unwind the unwound threads by rotating the stranded tube relative to the tube tool in the direction of winding. Furthermore, the tube tool may be operated for unwinding wound coiled threads and rewinding unwound threads. Moreover, the tube tool may be operated for unwinding a proximal portion end of the stranded tube or for unwinding a distal portion end of the stranded tube. In addition, the tube tool may be operated for passing an unwound thread from a tube tool proximal portion to a tube tool distal portion, and vice versa. Likewise, the tube tool may be provided with one or more tool thread duct(s), and such a thread duct may support a distal thread extremity of an unwound thread in at least one tube tool thread duct. A distal thread extremity may protrude distally out of the tube tool thread duct and a thread retention may prevent proximal retrieval of the distal thread extremity of the thread out of the tube tool duct.

It is one further object of the present invention to provide a handling and manipulation shaft having a lumen and to dispose the tube tool in a distal portion of the lumen.

It is another object of the present invention to provide a system operable for anchoring of and into at least one corpus which is disposed distally in a conduit, where the system includes a handling and manipulation shaft and a stranded tube having a plurality of wound coiled threads and a longitudinal axis. The system further includes a tube tool which is associated with the stranded tube and which is navigated together therewith by the handling and manipulation shaft into engagement with the corpus. The tube tool is configured to unwind one or more wound coiled thread(s) as one or more unwound coiled thread(s) by relative rotation of the tube tool against the stranded tube, where the unwound coiled thread(s) of the stranded tube are configured for anchoring of and into the corpus.

It is yet another object of the present invention to provide a system wherein the tube tool is configured to unwind the unwound threads in rotation along an unwound thread longitudinal axis which is disposed at an angle relative to the longitudinal axis of the stranded tube. Furthermore, the tube tool has a plurality of tube tool thread ducts which are oriented at a duct angle relative to the longitudinal axis for control of the angle between the longitudinal axis and the unwound thread longitudinal axis.

It is still another object of the present invention to provide a system wherein the stranded tube proximal portion end of the stranded tube is coupled in releasable attachment relative to the handling and manipulation shaft and to the tube tool, which attachment is released by proximal retrieval of the handling and manipulation shaft. Moreover, the uncoupled and unwound stranded tube is configured as a fastener operative for anchoring the corpus. Furthermore, a driven ring is fixedly coupled to the proximal end portion of the stranded tube, and the driven ring is operative as a support for an implement.

It is a final object of the present invention to provide a system wherein the unwound stranded tube is configured to anchor a physical body.

BRIEF DESCRIPTION OF DRAWINGS

Non-limiting embodiments of the invention will be described with reference to the following description of exemplary embodiments, in conjunction with the figures. The figures are not shown to scale and any measurements are only meant to be exemplary and not necessarily limiting. The figures are schematic, for use to describe principles and concepts. In the figures, identical structures, elements, or parts that appear in more than one figure are preferably labeled with a same or similar number in all the figures in which they appear, in which:

FIGS. 21 to 24 detail proximal unwinding and anchoring of a corpus,

FIGS. 41 to 44 are enlarged photographs of the unwinding process.

DESCRIPTION OF EMBODIMENTS

Unwinding a Stranded Tube

Figure 4:
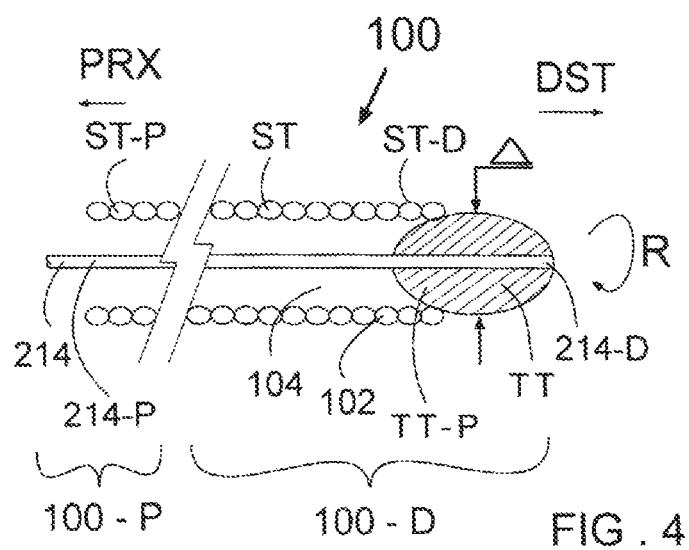
FIG. 4 shows a simplified embodiment of a device.

FIG. 4 schematically exemplifies an embodiment 100 of a system having a stranded tube ST and a tool tube TT, which form a mechanism for unwinding the stranded tube. As shown in FIG. 4, the embodiment 100 has a proximal portion 100-P shown partially, and a distal portion 100-D. A tool tube TT is fixedly coupled to the distal end portion 214-D of the wire 214 which extends from the proximal portion 100-P to the distal portion 100-D. The wire 214 passes longitudinally through the lumen 104 of the stranded tube ST. The wire 214 and the stranded tube ST may be manipulated from the proximal portion 100-P of the embodiment 100, although shafts for handling and manipulation HMA are not shown in FIG. 4. The proximal portion 100-P may be selected as a catheter or another device known in the art for supporting and allowing command and control of the distal portion 100-D. For the anchoring of and into at least one corpus COR disposed distally in a conduit BV it is first necessary to provide a stranded tube ST having a plurality of prestressed tightly wound helically coiled threads 102 and to navigate the stranded tube for distal engagement with the at least one corpus. Handling and manipulation shafts HMA for navigation in conduits, are well known in the art, and may be configured for the navigation of the stranded tube ST and of the tube tool TT, to engage the corpus COR. Second, at least one wound coiled thread 102 out of the plurality of wound coiled threads of the stranded tube ST is unwound as at least one unwound thread 105. Third comes the anchoring of the at least one unwound thread 105 into the at least one corpus COR.

Distal DST refers to the direction of the corpus COR disposed distally in the conduit BV, while proximal or PRX indicates the opposite direction, away from the corpus, thus pointing towards an operator standing away from the conduit, which operator is not shown.

Figure 1:
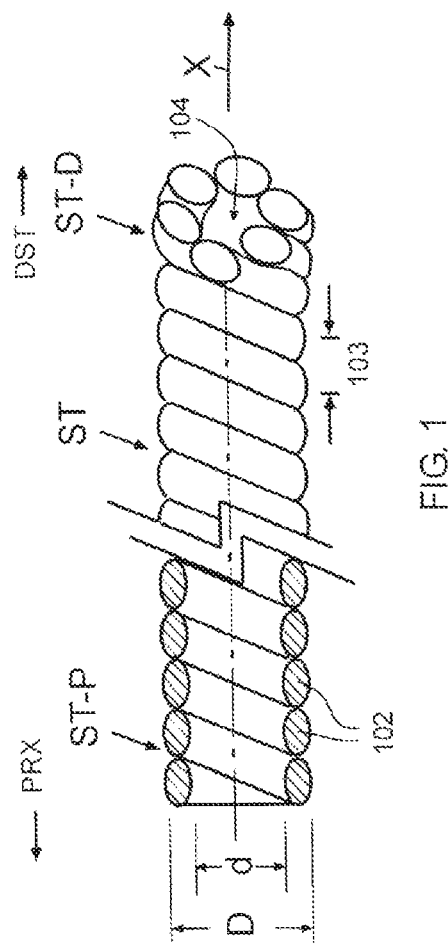
FIG. 1 shows a stranded tube.

In FIG. 4, the tool tube TT is shown disposed in abutment with the distal portion end ST-D of the stranded tube ST, where at least a proximal portion TT-P of the tube tool penetrates the stranded tube lumen 104, which is shown in FIG. 1. The proximal portion end ST-P of the stranded tube ST, which has a direction of winding of the wound threads 102, may be rotated in the winding direction, as shown by the arrow R, and may be urged or pushed distally against the tool tube TT while the wire 214 is held stationary. The rotation of the stranded tube ST relative to the stationary tool tube T will unwind at least one wound thread 102 of the distal portion end ST-D of the stranded tube. The helically coiled wound threads 102 may be liberated as at least one or as a plurality of helically coiled unwound threads 105, which are not shown in FIG. 4. It is the friction developed by longitudinal force application and relative rotation between the stranded tube ST and the tube tool TT that suffices to unwind the distal portion end ST-D of the stranded tube.

In other words, the unwinding of the wound coiled threads 102 requires the provision of a tube tool TT, which is engaged in relative rotation in the direction of winding of the stranded tube ST, and the longitudinal alignment of the tube tool TT and of the stranded tube ST. It is the operation of the tube tool TT in longitudinal force application and relative rotative association with the stranded tube ST that unwinds wound threads 102. Hence, it is the relative rotation between the stranded tube ST and the tube tool TT that unwinds wound threads 102 into unwound threads 105.

In the exemplary embodiment 100 of FIG. 4, the tool tube TT has an exterior diameter that may be smaller than the exterior diameter D of the stranded tube ST, but has to be larger than the interior diameter d of the stranded tube ST. Both the exterior diameter D and the interior diameter d are shown in FIG. 1.

Figure 5:
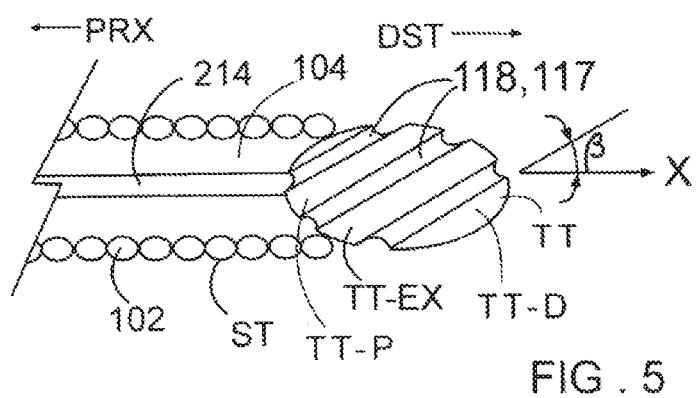
FIGS. 5 to 7 depict embodiments of a tube tool.

To facilitate unwinding of the stranded tube ST, an embodiment of the tube tool TT shown schematically in FIG. 5, may have thread ducts 117, such as grooves 118. The grooves 118 may be disposed on an exterior surface T-EX of the tube tool TT and may be configured to help unwind wound coiled threads 102 and to guide and orient the unwound thread(s) 105. Furthermore, the grooves 118 may be disposed at a duct angle β relative to the wire 214. The angle β may range from zero, thus parallel to the wire 214, to a selected positive or negative angle. The duct angle β is measured relative to the wire 214, which is coaxial with the longitudinal axis X of the stranded tube ST that is co-aligned with the tube tool TT. In addition, the grooves 118 may be curvilinear if so desired. In an embodiment, to even further facilitate unwinding of the stranded tube ST, the distal end 108 of the unwound threads 105 may be readily unwound and disposed a priori in the grooves 118, as shown schematically in FIG. 6.

It is noted that the thread ducts 117 or grooves 118 of the tube tool T provide passage for an unwound thread 105 from a tube tool proximal portion TT-P to a tube tool distal portion TT-D. Furthermore, at least one or a plurality of coiled threads 102, which have a distal thread extremity 108, may be unwound and disposed in a groove 118 prior to engagement with the corpus COR. Thus, at least one tube tool thread duct 117, or groove 118, may support the distal thread extremity 108 of an unwound coil 105.

Engagement of the unwound threads 105 with the corpus COR refers to the disposition of unwound threads into place or in a selected position for permitting their anchoring of and into the corpus.

Figure 7:
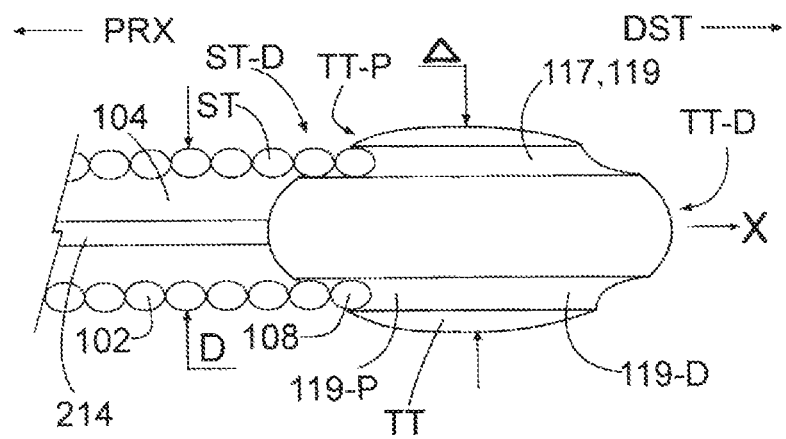

In an embodiment shown schematically in FIG. 7, the exterior diameter Δ of the tube tool TT is larger than the exterior diameter D of the stranded tube ST. Tube tool thread ducts 117, shown as closed tube tool conduits 119 passing through the interior of the tube tool TT, may be disposed as passages opened parallel or at an angle relative to the axial length of the tube tool TT, stretching from the tube tool proximal portion TT-P to the tube tool distal portion TT-D. The axial length of the tube tool TT is co-aligned with the axial length X of the stranded tube ST. The tube tool conduits 119 may be disposed either longitudinally as shown in FIG. 7, or as not shown in the Figs., at an angle relative to the wire 214, or be curved. Only two tube tool conduits 119 are shown in FIG. 7 for the sake of clarity.

The tube tool conduits 119 are configured to unwind the wound and coiled threads 102, to permit passage therethrough of the unwound and coiled threads 105, and to guide and orient the unwound coiled threads 105.

In operation, the distal portion end ST-D of the stranded tube ST abuts forcefully and longitudinally against the proximal portion TT-P of the tube tool TT. Next, the wound threads 102 may be unwound by relative rotation of the proximal portion end ST-P of the stranded tube ST in the winding direction thereof while the wire 214, and thus also the tube tool TT, are held stationary. The wound threads 102 are unwound and are forced to pass through the conduits 119, to then exit out of the tube tool distal portion TT-D as unwound threads 105. If desired, the distal portion ST-D of the stranded tube ST may be partially unwound for introduction of the distal end 108 of at least one unwound thread 105 into the proximal portion 119-P of the conduits 119.

Figures 11, 12:
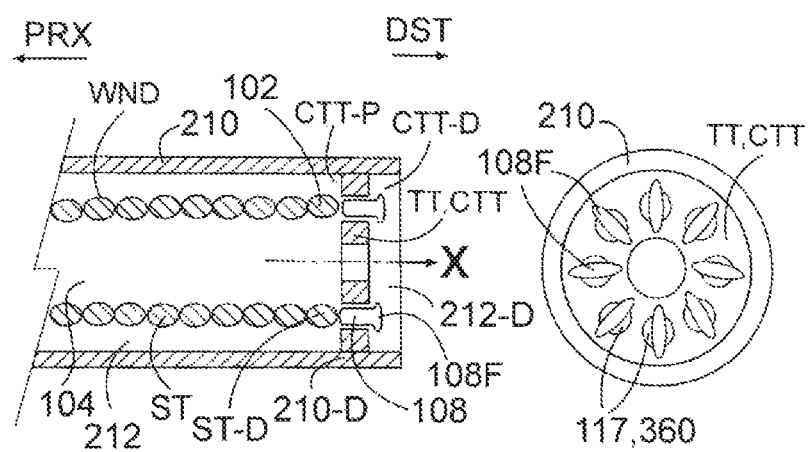
FIGS. 11 and 12 show an embodiment of a tube tool.

Alternatively, the distal ends 108 may be disposed in and through the conduits 119 to reach the distal portion 119-D of the conduits 119. If desired, but not shown in Fig. one or more distal ends 108 may slightly protrude distally out of the conduits 119. This means that at least one distal thread extremity 108 of the unwound coiled threads 105 may be disposed in a respective conduit 119 and protrude thereout prior to engagement with the corpus COR. Furthermore, the at least one distal thread extremity 108 may have a thread retention means 108F, which is configured to prevent proximal retrieval of the distal thread extremity 108 out of the tube tool thread duct 117 or tube tool conduit 119. A distal thread retention means 108F is shown in FIG. 11, for example as a flattening of the distal end 108 of the unwound coiled threads 105.

The configuration of the tube tool TT allows the tube tool thread ducts 117, or tube tool conduit 119 not only to unwind wound threads 102, but also to rewind unwound threads 105 back into a tightly wound stranded tube ST. Rotation of the stranded tube ST contrary to the winding direction of the stranded tube will rewind the liberated unwound threads 105 and rebuild the stranded tube back into a tightly wound structure. Thereby, the tube tool TT is operable for unwinding the wound and coiled threads 102 and for rewinding of the unwound coiled threads 105.

Figures 8, 9:
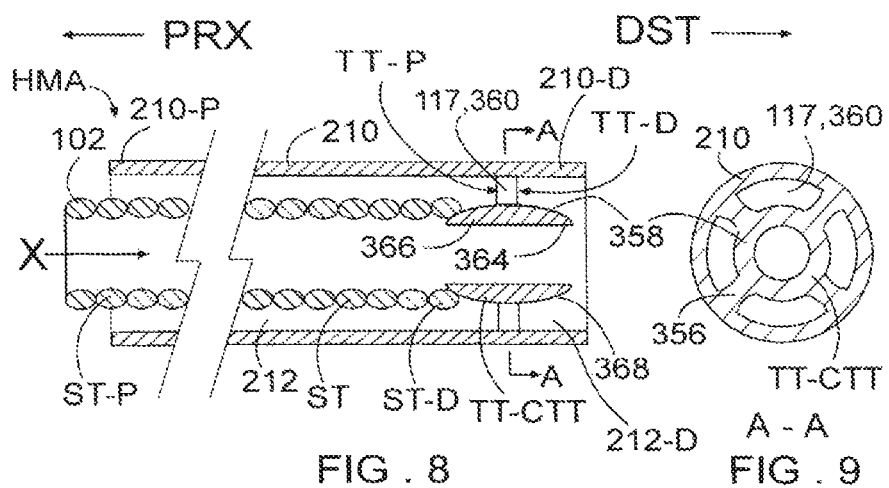
FIGS. 8 to 10 illustrate a simplified exemplary embodiment.
Figure 10:
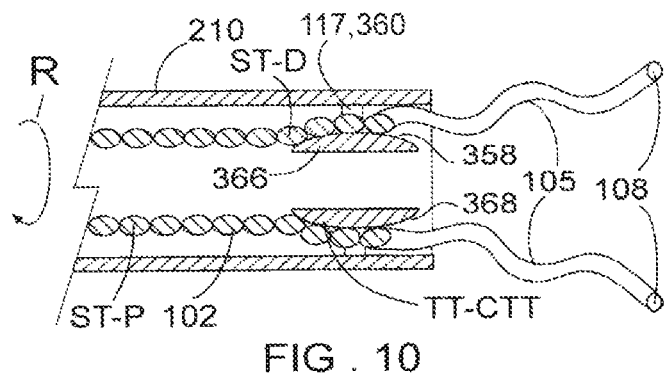

FIGS. 8 to 10 schematically illustrate an embodiment of a tube tool TT supported by a shaft 210, or catheter 210. The shaft 210, coaxial with and exterior to the stranded tube ST, has a shaft proximal portion 210-P and a shaft distal portion 210-D. A shaft lumen 212 extends throughout the length of the shaft 210. The tube tool TT, or catheter tube tool CTT, may be supported at the shaft distal portion 210-D in the interior of the shaft lumen distal portion 212-D. The stranded tube ST may be disposed coaxially in the shaft lumen 212 of the shaft 210, and may stretch from the shaft proximal end 210-P up to the abutment of the distal portion end ST-D of the stranded tube with the tube tool TT.

FIG. 9 is a cross-section A-A cut in FIG. 8 through the shaft distal portion 210-D supporting the tube tool TT, showing details of the tube tool. The tube tool TT may be supported distally in the shaft lumen 212 of the shaft 210 by a plurality of radially extending legs 356 that support a central sleeve 358, which central sleeve is concentric with the shaft. A plurality of ducts 117 or tool openings 360 may be disposed intermediate between the plurality of legs 356 to provide passage from the proximal side TT-P to the distal side TT-D of the tube tool TT. In other words, the tube tool TT may include a plurality of thread ducts 117, or duct openings 360 that may be disposed intermediate between the shaft 210 and the central sleeve 358 to form the legs 356 therebetween.

The tube tool TT may have a selected number of duct openings 360, which openings may have a geometrical shape chosen according to practical needs, such as for example the circular shape of a bore, which example is not shown in FIG. 9. The duct openings 360 shown in FIG. 8 may be disposed at an angle β relative to the axis X of the stranded tube ST, however, the angle β is not shown in FIGS. 8 to 10.

The central sleeve 358 is configured to operate in association with the tube tool openings 360 to unwind wound threads 102 for passage thereof from the proximal portion TT-P to de distal portion TT-D as unwound threads 105.

In FIGS. 8 and 9, the central sleeve 358 is shown to have a cross-section profile resembling the profile of a wing, where the leading edge 364 may be oriented toward the distal direction DST and the trailing edge 366 may point to the proximal direction PRX. The legs 356 are attached to the shaft 210 and to the extrados 368 of the central sleeve 358. Such a configuration of the tube tool TT, or catheter tube tool CTT, allows the tube tool openings 360 not only to unwind wound threads 102, but also to rewind unwound threads 105 back into a wound stranded tube ST. Rotation of the stranded tube ST contrary to the winding direction of the stranded tube will rewind the liberated unwound threads 105 and rebuild the stranded tube back into a tightly wound structure. Thereby, the tube tool TT is operable for unwinding the wound and coiled threads 102 and for rewinding of the unwound coiled threads 105.

FIG. 10 schematically depicts unwinding of the wound threads 102 by rotation initiated at the proximal portion end ST-P of the stranded tube ST. Rotation in the winding direction R of the stranded tube ST and longitudinal drive of the distal portion end ST-D towards the central sleeve 358 push the wound threads 102 to abut onto the trailing edge 366 of the catheter tube tool TT, or CTT. Thereby, the stranded tube ST is unwound when reaching the tube tool distal end portion TT-D and the unwound threads 105 exit distally through the tool openings 360. Only two unwound threads 105 are shown to keep FIG. 10 simple.

If desired, the distal portion end TT-D of the catheter tube tool CCT may support initially unwound threads 105 emerging out of the tube tool thread ducts 117, or tube tool openings 360, that are disposed a priori in the tube tool openings to ease further unwinding of the stranded tube ST.

FIGS. 11 and 12 schematically illustrate an embodiment of a tube tool TT, or catheter tube tool CTT, configured as a disk having a plurality of circular tool openings 360. The tube tool openings 360 are not necessarily circular and may be selected to have any practical geometric shape. The tube tool TT is shown in FIG. 12 as a front elevation of FIG. 11 as seen from the distal direction DST toward the proximal direction PRX. The catheter tube tool CTT may be disposed in oblique or, as shown in FIGS. 11 and 12, perpendicular to the longitudinal direction of the shaft 210, at the distal end 210-D. The wound threads 102 at the distal portion end ST-D are shown with their respective thread distal ends 108 already engaged in the tool openings 360. It is noted that the distal end 108 of the unwound threads may be flattened to form flat ends 108F, to prevent proximal retraction of the unwound threads 105 back to the proximal side CTT-P of the catheter tube tool CTT. Such proximal retraction prevention means do not impede the anchoring performance of the unwound threads 105 for the anchoring of and into the corpus COR. For anchoring a corpus COR, the stranded tube ST is first disposed in engagement therewith. Then, when in appropriate engagement disposition, the stranded tube ST is rotated in the winding direction thereof, and pushed against and to the tube tool TT, or catheter tube tool CTT. In result thereof, unwound threads 105 will exit out of the tube tool openings 360, and extend distally away for the anchoring of and into the corpus COR, which is not shown in FIGS. 11 and 12.

It is understood that engagement of the wound stranded tube ST with the corpus COR before unwinding, may mean proximal or distal disposition of the stranded tube next to or close to the corpus, or in abutment with the corpus, and may also mean disposition in the interior of the corpus.

In FIGS. 10 and 11, the distal thread extremities 108 are disposed in distal protrusion out of the ducts 117 or tube tool openings 360, prior to engagement with the corpus COR. At least one distal thread extremity 108 out of the plurality of wound threads 102 may be disposed to protrude distally out on the side CTT-D of the catheter tube tool CTT through least one tube tool opening 360 out of the plurality of tube tool openings. It suffices for at least one thread extremity 108 to have a distal thread retention means 108F that is configured to prevent proximal retrieval thereof to the proximal side CTT-P of the catheter tube tool CTT, through the at least one tube tool opening 360, to prevent proximal retrieval of the stranded tube ST. Furthermore, the tube tool TT may be operated to unwind wound coiled threads 102 and to rewind unwound coiled threads 105 back into a stranded tube ST of tightly wound coiled threads, as described hereinabove with respect to FIGS. 8 and 9.

The tube tool TT may be made out of metal, plastic material, natural material or synthetic material, or out of a combination of materials.

Figure 13:
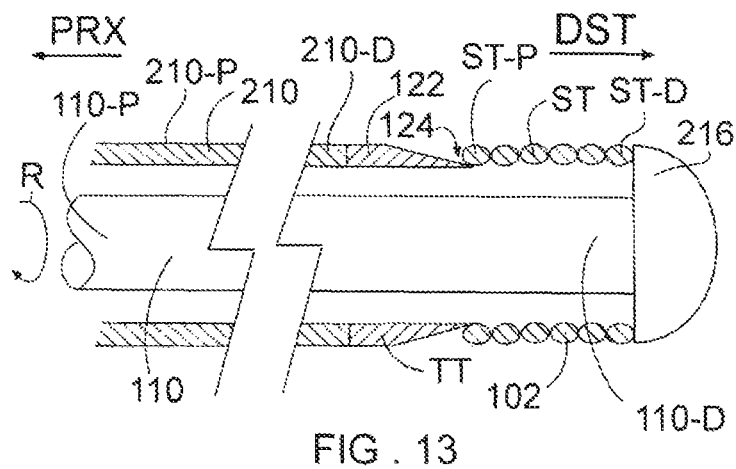
FIGS. 13 and 14 depict proximal unwinding.

FIG. 13 schematically illustrates an exemplary embodiment configured to unwind the proximal portion ST-P of the stranded tube ST. In FIG. 13, a wire 110 has a wire distal end 110-D that is fixedly coupled to a nose tip 216, say by welding for example, or by other means known to those skilled in the art. The nose tip 216 is fixedly coupled to the distal portion ST-D of the stranded tube ST, for example by welding if so desired. The wire 110 extends from the wire distal end 110-D to a wire proximal end 110-P. The stranded tube ST coaxially surrounds the wire distal end 110-D. A shaft 210 that coaxially surrounds the wire 110 has a proximal portion end 210-P and a distal portion end 210-D. The distal portion end 210-D is fixedly coupled to a tube tool TT that may be configured as a hollow cylinder or tube terminated distally by a hollow conical portion 122, or hollow cone frustum 122, which may slant distally to terminate as a rim 124. The proximal portion ST-P of the stranded tube ST abuts the rim 124.

To unwind the stranded tube ST, the rim 124 is pushed in abutment with the proximal portion ST-P of the stranded tube. For unwinding, the wire 110 may be rotated in the winding direction R of the stranded tube ST, whereby the nose tip 216 and the stranded tube are also rotated, while the proximal portion end 210-P of the shaft 210 and thus also of the hollow cone 122 may be held stationary. The relative rotation of the rim 124 of the hollow conical portion 122 of the tube tool TT which is pushed against the proximal portion ST-P of the stranded tube ST liberates and unwinds the wound threads 102. These wound threads 102 unwind in proximal direction PRX as unwound threads 105.

Figure 14:
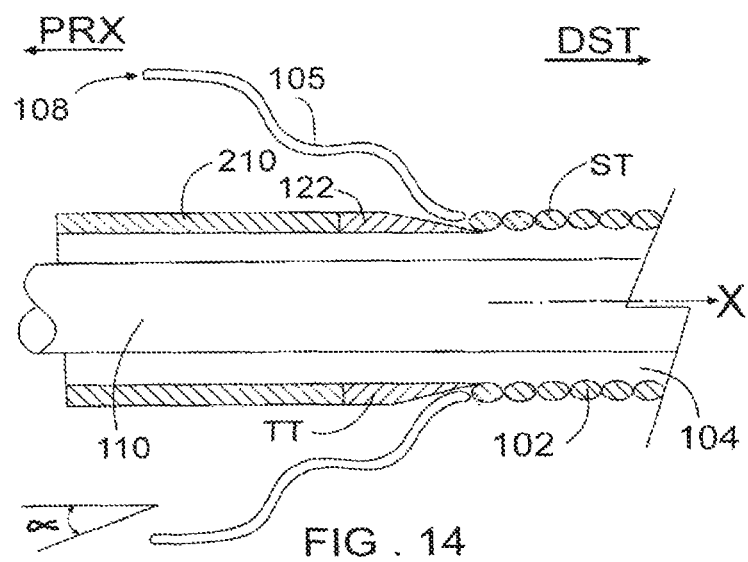

FIG. 14 schematically depicts the unwinding of the wound threads 102 out of the stranded tube ST, clearly showing the corkscrew-shape of the liberated unwound coiled threads 105. The unwound coiled threads 105 may form an angle α with the longitudinal axis X of the stranded tube ST. The angle α may be controlled for example by the shape and the angle of the hollow cone frustum 122 and by mechanical parameters of the stranded tube ST. Such mechanical parameters of the stranded tube ST may include for example, the pre-stress of the wound threads 102, and the type of material of the stranded tube. Only two coiled threads 105 are shown in FIG. 14 for the sake of clarity.

It has thus been described hereinabove that unwinding the wound and coiled threads 102 includes operating a tube tool TT or CTT at the proximal portion end ST-P or at a distal portion end ST-D of the stranded tube ST. In other words, a tube tool TT, or a catheter tube tool CTT, may be disposed proximal the stranded tube ST for unwinding in the proximal direction, or distal the stranded tube for unwinding in the distal direction. Moreover, the tube tool TT or CTT may be disposed at least partially in the interior of the lumen 104 of the stranded tube ST.

Engagement of a Corpus

For the anchoring of and into a corpus COR, a stranded tube ST may be unwound either distally or proximally. Unwinding of the stranded tube ST may be initiated in various anchoring engagement dispositions of the stranded tube relative to the corpus COR. Prior to anchoring into the corpus COR, the stranded tube ST and the tube tool TT or CTT, have to be navigated into mutual anchoring engagement disposition. Navigation means passage up to the corpus COR through the system of conduits BV, such as a vasculature for example.

FIGS. 15 to 20 schematically illustrate relative anchoring engagement dispositions of the stranded tube ST for the anchoring of and into a corpus COR, for example by distal unwinding of the stranded tube. The corpus COR is shown disposed in the interior BVIN of a conduit BV having vessel walls VW, such as for example of a blood vessel. In FIGS. 15 to 20, only the stranded tube ST, the corpus COR, and the conduit BV are shown, but not the tube tool TT, or CTT, for the sake of clarity.

Figure 15:
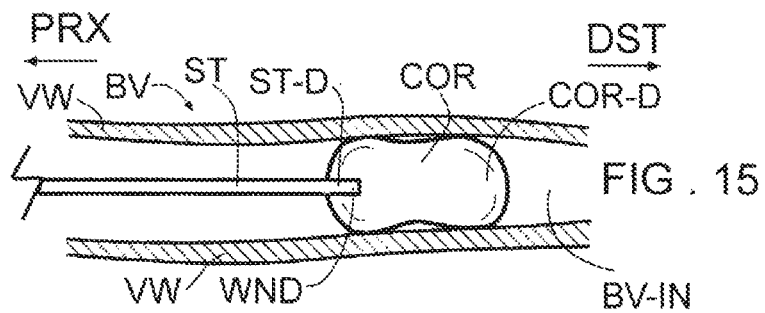
FIGS. 15 to 20 illustrate distal unwinding and capture of a corpus.

In FIG. 15, the distal portion end ST-D of the unwound stranded tube ST is shown engaged in proximal penetration into the penetrable corpus COR after having been navigated therein, for example by a catheter or by means known to those skilled in the art. The stranded tube ST may now be unwound distally from a first wound state WND shown in FIG. 15, to a second unwound state UNW shown in FIG. 16.

Figure 16:
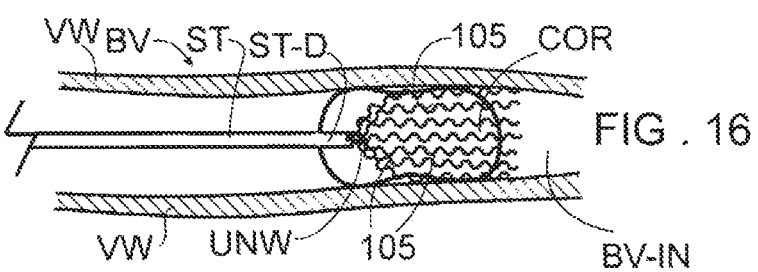

In FIG. 16, one or a plurality of wound threads 102 has been unwound into distal and radial expansion as unwound threads 105. Unwinding calls for operation with the tube tool TT, which is not shown in FIGS. 15 to 20. By the unwinding relative rotation of the stranded tube ST, the unwound threads 105 are distally "corkscrewed" into the penetrable corpus COR for firm anchoring thereof and therein. Now that anchoring of and into the corpus COR is achieved by at least one unwound thread(s) 105 extending in distal and radial fanned-out embedment in the interior of the corpus, the morphology of the corpus is structurally reinforced. Such a structural reinforcement by fanned-out embedment in the corpus COR prevents the occurrence of fragmentation during proximal retrieval of the corpus out of a conduit BV.

It is noted that the at least one unwound coil(s) 105 may anchor at least into a proximal portion of the corpus, into most of or the entirety of the length of the corpus COR, and even continue and exit distally out of the corpus, although not shown as such in the Figs.

Hence, anchoring of a corpus COR includes unwinding of at least one coiled thread 102 out of the plurality of wound threads 102 into one or a plurality of unwound threads 105 that may fan-out in expansion away from the stranded tube ST. The expansion and fanning-out of at least one unwound thread 105 in the corpus COR adds structural reinforcement to the corpus and prevents fragmentation thereof. The stranded tube ST unwound for anchoring of and into the captured corpus COR may now be retrieved proximally for removal out of a conduit BV or vasculature for example. If desired, proximal retrieval of the corpus COR may be achieved initially by proximal retrieval of the stranded tube ST and be followed for example by aspiration of the corpus.

In the embodiments of the present invention, proximal retrieval of the corpus COR may be achieved by proximal retrieval of the stranded tube ST and/or with a portion of, and/or with the entire handling and manipulation shaft HMA.

The stranded tube ST anchoring the corpus COR may be retrieved proximally out of the conduits BV, vasculature or system, by proximal retrieval of the stranded tube ST or of the same mechanical handling and manipulation shaft HMA used for the engagement with the corpus COR. Alternatively, aspiration apparatus may be disposed proximally away from the corpus COR where the conduits BV, or blood vessels, are wider and able to accommodate an aspiration instrument. This means that the stranded tube ST first engages the corpus COR, then anchors therein, and finally retrieves the corpus proximally to a wider portion of the conduit BV or vasculature, where an aspiration device may be disposed and operated to removes the corpus out of the system of conduits.

Figure 17:
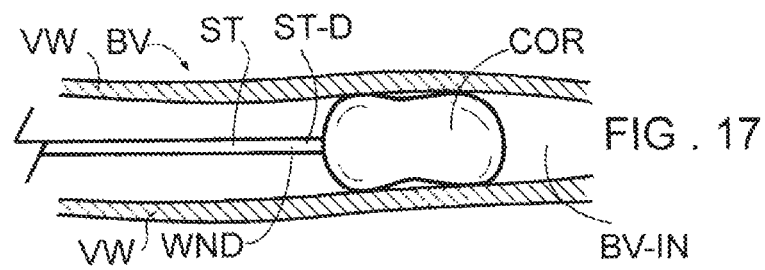

In FIG. 17, the unwound stranded tube ST is shown engaged in proximal abutment with the penetrable corpus COR after having been navigated thereto. Even though not shown in FIG. 17, the following is also true for a stranded tube ST proximally engaged close to or disposed in proximal engagement proximity with the corpus COR. The stranded tube ST may now operate on, or be operated upon, by the tube tool TT to unwind distally from a first wound state WND shown in FIG. 17, to a second unwound state UNW shown in FIG. 18. Unwinding calls for operation in association with the tube tool TT, which is not shown in FIGS. 15 to 20.

Figure 18:
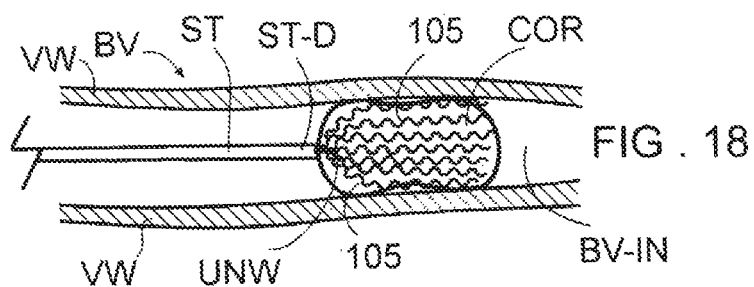

In FIG. 18, the one or plurality of wound threads 102 have been unwound into distal expansion, and may diverge radially as unwound threads 105. In response to the unwinding relative rotation of the stranded tube ST, the unwound threads 105 distally "corkscrew" into the penetrable corpus COR. Now that anchoring of and into the corpus COR is achieved by at least one unwound thread(s) 105 extending in distal and radial fanned-out embedment, the morphology of the corpus is structurally reinforced. Such a structural reinforcement by fanned-out embedment in the corpus COR prevents the occurrence of fragmentation during proximal retrieval of the corpus out of a conduit BV. The stranded tube ST anchoring the corpus COR may now be retrieved proximally or if desired or necessary, by help of an aspiration device or another corpus retrieval device disposed proximally away.

It is noted that the at least one unwound coil(s) 105 may have a proximal portion which is deployed proximal to the corpus COR, and a portion that is anchored at least into a proximal portion of the corpus. Furthermore, the at least one unwound coil(s) 105 may be anchored into most of or in the entirety of the length of the corpus COR, and even continue and exit distally out of the corpus, although not shown as such in the Figs.

Figure 19:
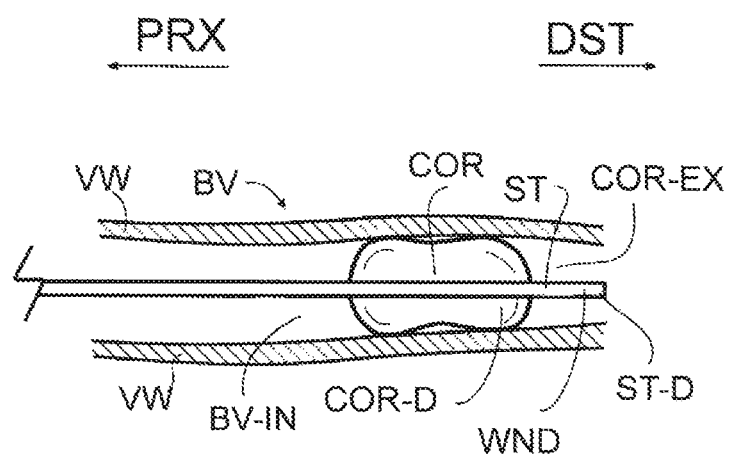

In FIG. 19, the distal portion end ST-D of the unwound stranded tube ST is shown engaged distally, just out to the exterior COR-EX of the penetrable corpus COR, after having been navigated therethrough. The stranded tube ST may now operate or be operated upon by the tube tool TT to unwind distally from a first wound state WND shown in FIG. 19, to a second unwound state UNW shown in FIG. 20.

Figure 20:
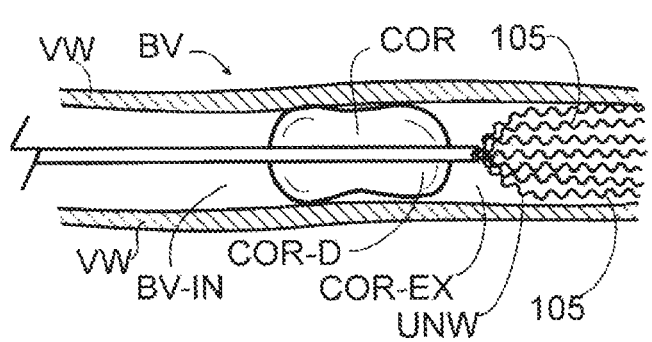

In FIG. 20, the wound threads 102 have been unwound into distal and radial expansion as unwound threads 105. Unwinding calls for the operation of the tube tool TT or CTT, which is not shown in FIGS. 15 to 20. In response to the unwinding relative rotation of the stranded tube ST, the unwound threads 105 "corkscrew" distally out of the distal portion COR-D, thus distally out and away from the penetrable corpus COR. The distally and sometimes radially fanned-out one unwound thread 105 or plurality of unwound threads is configured to engage the corpus COR when the stranded tube ST is retrieved proximally, and to drive or drag the corpus proximally. The corpus COR may thus be removed out of the conduit BV, or vasculature, when the stranded tube ST is retrieved proximally. If desired or necessary, an aspiration device or another corpus retrieval device may be of help for further retrieval.

Hence, the unwound stranded tube ST may be engaged in relation with the corpus COR in a disposition proximal to the corpus, or in a disposition in the interior of the corpus, or in a disposition distal to the corpus, for corpus retrieval or for corpus fastening purposes, as described hereinbelow.

FIGS. 21 to 24 schematically illustrate the relative anchoring engagement of the stranded tube ST for anchoring of and into a corpus COR by proximal unwinding of the stranded tube. The corpus COR is shown disposed in the interior BVIN of a conduit BV having conduit vessel walls VW, such as a blood vessel for example. In FIGS. 21 to 24 inclusive, only the shaft 210, the stranded tube ST, the corpus COR, and the conduit vessel BV are shown. The tube tool TT, or CTT, and other elements are not shown in FIGS. 21 to 24 for the sake of clarity.

In FIG. 21, the unwound stranded tube ST is shown disposed distally to the shaft 210 and in engagement with the interior COR-IN of the corpus COR after penetration therein. The stranded tube ST may now be operated to unwind proximally from a first wound state WND shown in FIG. 21, to a second unwound state UNW shown in FIG. 22.

In FIG. 22, the wound threads 102 have been unwound into proximal expansion as at least one or a plurality of unwound thread(s) 105. Unwinding requires operation of the tube tool TT, which is not shown in FIGS. 21 to 24. In response to the relative unwinding rotation of the stranded tube ST, the unwound threads 105 are "corkscrewed" proximally into the penetrable corpus COR. Now that anchoring of and into the corpus COR is achieved by at least one unwound thread(s) 105 extending in proximal and radial fanned-out embedment, the morphology of the corpus is structurally reinforced. Such a structural reinforcement by fanned-out embedment in the corpus COR prevents the occurrence of fragmentation during proximal retrieval of the corpus out of a conduit BV. The stranded tube ST anchoring the corpus COR may now be retrieved proximally or if desired or necessary, by further help of an aspiration device or another corpus retrieval device means disposed proximally away.

In FIG. 23, the unwound stranded tube ST is shown disposed distally to the shaft 210 and engaged distally, just out to the exterior COR-EX of the penetrable corpus COR, after having been navigated therethrough. The stranded tube ST may now be operated to unwind proximally from a first wound state UNW shown in FIG. 23, to a second unwound state WND shown in FIG. 24.

In FIG. 24, the at least one or plurality of wound thread(s) 102 have been unwound into proximal expansion as at least one or more unwound thread(s) 105. In response to the unwinding relative rotation of the stranded tube ST, the unwound threads 105 have been proximally "corkscrewed" into the penetrable corpus COR. Now that anchoring of and into the corpus COR is achieved by at least one unwound thread(s) 105 extending in proximal and radial fanned-out embedment, the morphology of the corpus is structurally reinforced. Such a structural reinforcement by fanned-out embedment in the corpus COR prevents the occurrence of fragmentation during proximal retrieval of the corpus out of a conduit BV. The stranded tube ST anchoring the corpus COR may now be retrieved proximally or if desired or necessary, by further help of an aspiration device or another corpus retrieval device disposed proximally away.

It is noted that the at least one unwound coil(s) 105 shown in FIG. 24 may have a distal portion which is deployed distal to the corpus COR, and a portion that is anchored at least into a distal portion of the corpus COR-D. Furthermore, the at least one unwound coil(s) 105 may be anchored into most of or the entirety of the length of the corpus COR, and even continue and exit proximally out of the corpus, although not shown as such in FIG. 24.

FIGS. 15 to 24 illustrate various examples of anchoring engagement of the stranded tube ST in relation with the corpus COR, including a disposition proximal to the corpus, a disposition interior to the corpus, and a disposition distal to the corpus. Proximal engagement in relation with the corpus COR includes disposition in proximal proximity to the corpus and in proximal abutment therewith. Distal engagement in relation with the corpus COR includes disposition in distal proximity to the corpus and in distal abutment therewith.

However, it is the mutually operative relation and association with the tool tube TT or catheter tube CTT that unwinds the stranded tube ST. Therefore, one may say that the tube tool TT may be engaged with and disposed relative to the corpus in a disposition proximal to the corpus, a disposition interior to the corpus, a disposition distal to the corpus, and a disposition where the tube tool is disposed at least in partial penetration into the lumen 104 of the stranded tube.

Exemplary Embodiments

Figure 25:
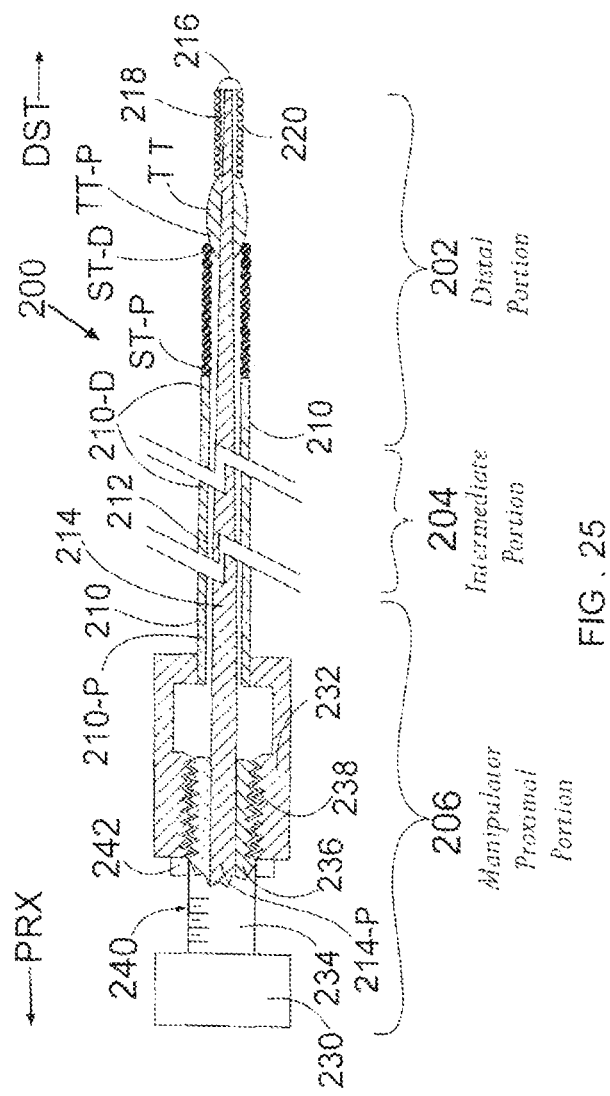
FIGS. 25 to 27 depict another embodiment.

FIG. 25 is an exemplary embodiment 200 showing a handling and manipulation shaft HMA supporting a device for the anchoring of and into a corpus COR, for example for retrieving a corpus out of a conduit BV such as a blood vessel. The embodiment 200 may have three main portions, namely a navigation distal portion 202, a navigation intermediate portion 204, and proximally, an actuator 206.

In FIG. 25, a hollow shaft 210 is shown to have a shaft lumen 212 wherethrough passes a wire 214. The shaft 210 and the wire 214 extend throughout from the device distal portion 202, via the navigation intermediate portion 204, to the proximally disposed actuator manipulation portion 206. Both the shaft 210 and the wire 214 may be made of stainless steel for example. A nose tip 216 fixedly coupled to the wire distal end 218 terminates the device distal portion 202. The nose tip 216 may have a smooth and convex distal surface configured for ease of insertion in the interior BVIN of a conduit BV. In the device distal portion 202, a helicoidal guidance spring 220 coaxial with the wire 214, is disposed intermediate the nose tip 216 and a tube tool TT. The guidance spring 220 may be made of stainless steel, or from radiopaque material, or may carry radiopaque markers for example. Furthermore, prior to insertion into a conduit BV and use, an operator, not shown in the Figs, may bend the guidance spring 220 into a desired shape.

The shaft 210 and the wire 214 may be considered as a handling and manipulation shaft HMA configured to navigate the stranded tube ST and the tube tool TT through conduits BV. Navigation devices HMA or handling and manipulation shafts HMA may thus be used to dispose the stranded tube ST in anchoring engagement relation with the corpus COR.

Figure 6:
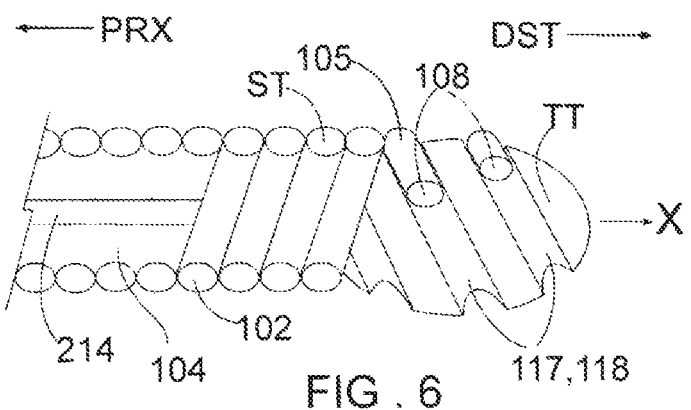

In an embodiment, the tube tool TT may have the shape of an ellipsoid, as already shown in FIG. 4, but, the embodiments of the tube tools 'I' described with reference to FIGS. 5 to 7 may be selected as practical options. The tube tool TT is fixedly coupled to the wire 214 intermediate between the guidance spring 220 and the stranded tube ST. The stranded tube ST shown in FIG. 1, is twisted out of a plurality of prestressed tightly wound helically coiled threads 102 made of natural or of artificial material, or of spring wires that are tightly coiled in gapless mutual contact with each other. The pitch 103 of the stranded tube ST may be selected as desired.

Figure 26:
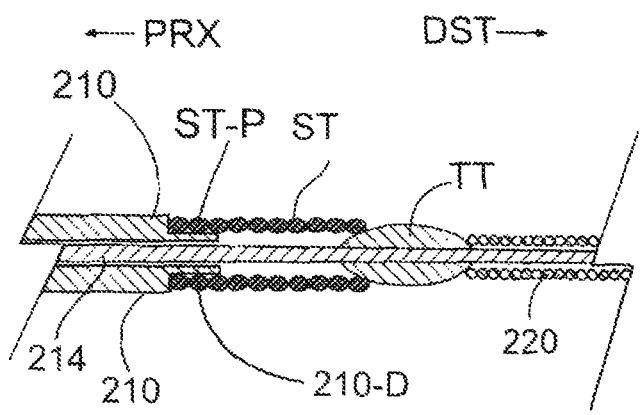

The stranded tube ST is shown coupled in co-coaxial longitudinal continuation of the shaft 210 and abuts the tube tool TT in alignment therewith. For example, the proximal portion end ST-P of the stranded tube ST may be welded to the distal portion 210-D of the shaft 210, or may be coupled thereto by means well known to those skilled in the art. In an embodiment, coupling of the proximal end portion ST-P to a recessed distal portion 210-D of the shaft 210 may be achieved by overlap, as shown in FIG. 26. The proximal end portion ST-P may overlap the recessed distal portion 210-D and be glued to, or welded to the distal portion 210-D of the shaft 210.

Pressure, friction and relative rotation in the winding direction exerted by the distal portion end ST-D of the stranded tube ST on the proximal portion TT-P of the tube tool TT suffices to unwind and separate the helicoidally wound threads 102. Mutual relative rotation in the winding direction of the stranded tube ST may be obtained by rotation of the stranded tube ST relative to the stationary tube tool TT, or by rotation of the tube tool TT relative to the stationary stranded tube ST, or by rotation of both the stranded tube ST and the tube tool TT in opposite direction. However, to unwind and liberate the helicoidally wound threads 102, the relative rotation has to occur in a same direction of rotation as the winding direction of the stranded tube ST.

FIG. 25 shows the actuator 206 that is used to operate the stranded tube ST for the anchoring of and into a corpus COR for example, for proximal retrieval out of a conduit BV. The actuator 206 has a wire handle 230 and a shaft handle 232. The wire handle 230 is fixedly coupled to the proximal wire portion 214-P of the wire 214, and the shaft handle 232 is fixedly coupled to the proximal shaft portion 210-P of the shaft 210. The wire handle 230 has a wire handle adaptor 234 disposed in longitudinal alignment with a male screw thread 236. The wire handle 230 is proximal to the wire handle adaptor 234 that is proximal to the male screw thread 236. The male screw thread 236 is configured for screwable engagement with a matching female screw thread 238 disposed in and pertaining to the shaft handle 232. The shaft handle 232 is configured to allow free rotation therein and thereout of the male screw thread 236. Hence, the male screw thread 236 is free to rotate in both clockwise and anti-clockwise directions. Likewise, the wire handle 230 is configured to allow free rotation over the male screw thread 236 in both clockwise and anti-clockwise directions. Moreover, the actuator 206 is configured to provide unhindered distal and proximal freedom of displacement for free relative rotation of the male screw thread 236 and of the female screw thread 238.

The wire handle adaptor 234 may be marked with a scale of wire handle graduations 240 shown partially only, to help the operator, not shown, to appreciate, for example, the relative disposition of the tube tool TT relative to the stranded tube distal portion ST-D. Furthermore, one or more out of the nose tip 216, the guidance spring 220, the tube tool TT, and the stranded tube ST may include one or more radiopaque marker(s) or be made out of material featuring radiopacity. If desired, a wire stopper 242 configured to stop relative motion of the wire 214 and of the shaft 210 may be coupled to the wire handle adaptor 234. The wire stopper 242 may be fixed to the wire handle adaptor 234 or may be operator-adjustable and be disposed as desired along the wire handle adaptor.

Figure 2:
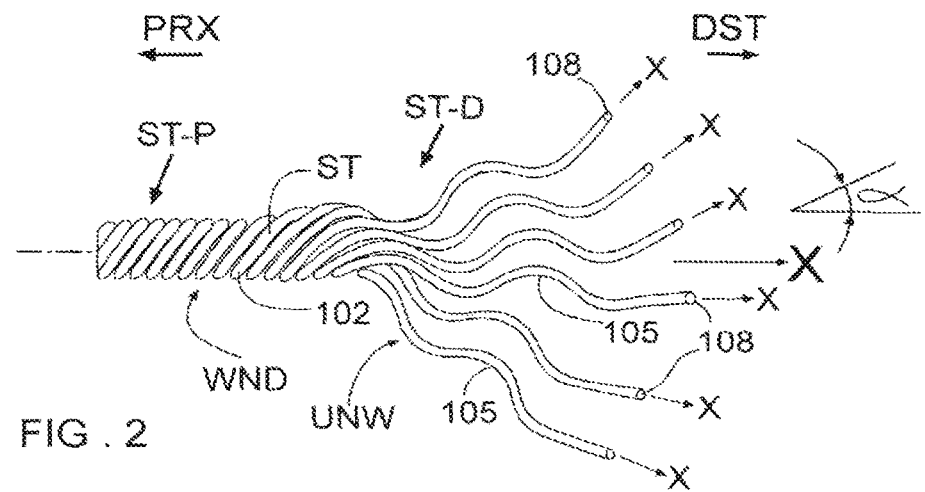
FIG. 2 depicts a stranded tube with an unwound distal end.
Figure 3:
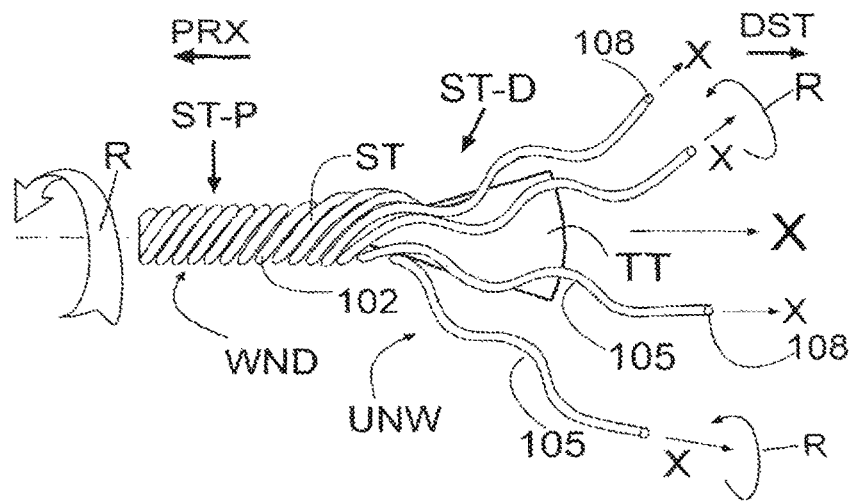
FIG. 3 illustrates a tube tool for unwinding a stranded tube.

To use the embodiment 200 shown in FIG. 25, for anchoring of and into a corpus COR, the stranded tube ST has to be engaged with the corpus and then unwound to liberate at least one, or a plurality, or the entirety of wound coiled thread(s) 102. Unwinding of the stranded tube ST liberates at least one, or a portion, or the plurality of the tightly prestressed helicoidal coiled and wound thread(s) 102. The wound threads 102 then separate and extend away from the stranded tube ST, possibly in radial direction, into unwound threads 105, as shown in FIG. 2. Parameters commanding the angle α of radial expansion of the unwound thread 105 may include the pitch distance 103, the material from which the stranded tube ST is made, the mechanical properties of the stranded tube ST such as dimensions and pre-stress of the threads 102, the shape of the tube tool TT, the configuration and the duct angle β of the tube tool thread ducts 117, 118, or 360, the exterior diameterΔ of the tube tool. The exterior diameterΔ of the tube tool TT is shown in FIG. 4.

Figure 27:
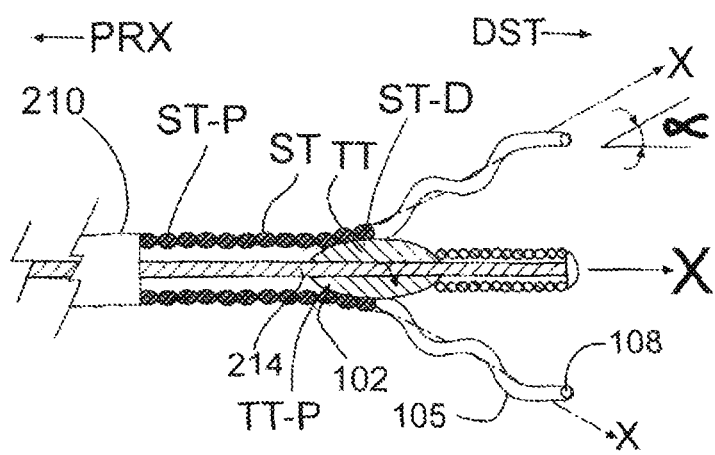

In FIG. 27 there is shown the distal portion end ST-D of the stranded tube ST, which is partially engaged over the proximal portion end TT-P of the tube tool TT. The wound threads 102 at the distal portion end ST-D have been unwound and liberated into unwound threads 105. Further liberation of the unwound threads 102 from their tight mutual contact requires further rotation in the winding direction of the stranded tube ST and force applied distally in the longitudinal direction of the stranded tube over the tube tool TT.

Reference is made to FIG. 25 regarding the use of the actuator 206 for the unwinding of the wound threads 102.

An operator, not shown, may first navigate the exemplary embodiment 200 for engagement of the stranded tube ST with the corpus COR. Navigation requires handling and manipulation shafts well known to those skilled in the art, such as a guiding catheter for example, which shafts are configured to support both the stranded tube ST and the tube tool TT. The term engagement herein means disposition of the stranded tube ST in operative relation with the corpus COR. Once the stranded tube ST is navigated to the corpus COR and engaged as desired, the operator may firmly hold the wire 214 stationary with one hand while rotating the shaft handle 232 with the other hand. Rotation of the shaft handle 232 rotates the stranded tube ST that is distally coupled thereto. Unwinding of at least one, or a portion, or the plurality of the tightly stranded wound threads 102 in association with the tube tool TT is obtained by rotation of the shaft handle 232 in the winding direction of the stranded tube ST. The winding direction of the stranded tube ST is the same direction as that of the thread windings of both the wire handle male screw thread 236 and of the shaft handle female matching screw thread 238.

As described hereinabove, first, the distal portion ST-D of the stranded tube ST is navigated to and engaged in relation with the corpus COR, which means that the stranded tube is disposed into the corpus COR, or in abutment with the corpus, or proximally or distally adjacent to the corpus. Distal unwinding was described hereinabove with reference to FIG. 20, and is accepted as referring to anchoring of the corpus COR.

Thereafter, the tube distal end ST-D is unwound to distally liberate the coiled wound threads 102 as unwound threads 105 configured for the anchoring of and into the corpus COR. It is the relative rotation of the stranded tube ST over the tube tool TT and about the axis X that causes each individual unwound thread 105 to rotate corkscrew-wise about its own respective axis x. Hence, the shaft handle 232 may be kept at standstill while the wire handle 230 is rotated.

Once at least one unwound threads 105 is engaged for anchoring of and into the corpus COR, this last one may be retrieved proximally away for removal out of the conduit BV. If desired, an aspiration device may be disposed proximally away for further help.

Figure 28:
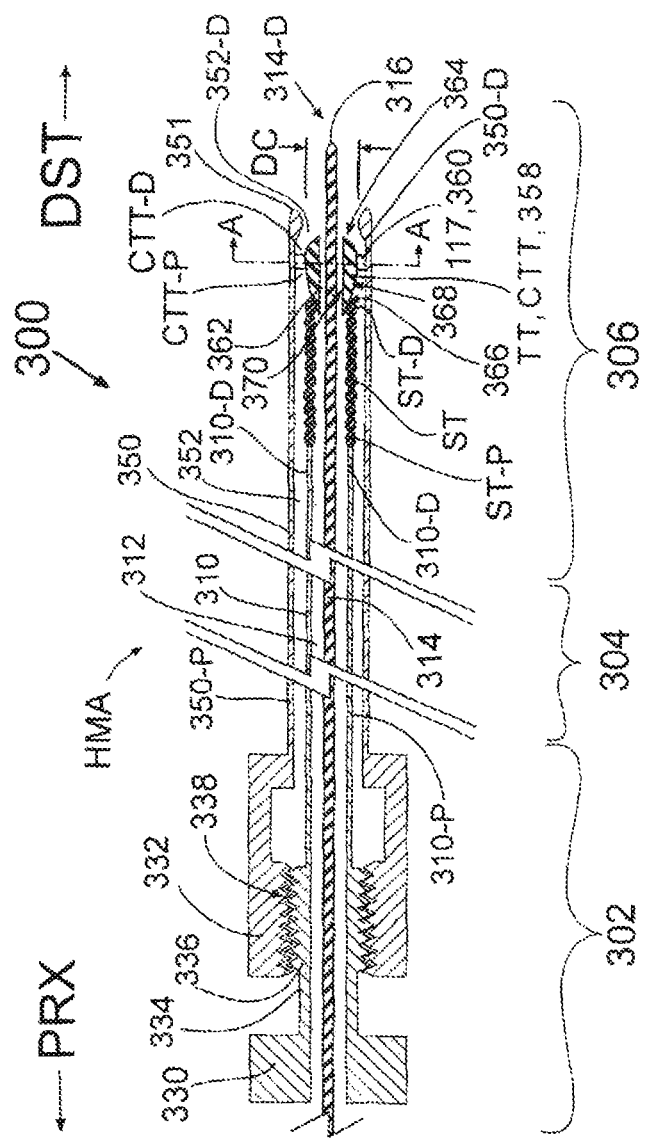
FIGS. 28 to 30 illustrate yet another embodiment.

FIG. 28 illustrates an exemplary embodiment 300 and a handling and manipulation shaft HMA for anchoring of and into a corpus COR, for proximal retrieval thereof for example. The embodiment 300 may include three main portions, namely a catheter distal portion 306, a catheter intermediate portion 304, and proximally, a catheter actuator 302.

In FIG. 28, a catheter 350 has a catheter lumen 352 wherethrough passes a hollow shaft 310 having a shaft lumen 312. The distal end portion 310-D of the shaft 310 may be coupled to the proximal end portion of the ST-P of the stranded tube ST as described with respect to the embodiment 200. The catheter distal portion 350-D may have a smooth rounded and convex catheter nose 351 configured for ease of insertion into a conduit BV, such as a blood vessel for example. The catheter 350 extends throughout from the catheter distal portion 306, via the catheter intermediate portion 304 to the catheter actuator 302 that is disposed proximally. A wire 314 passes throughout the shaft lumen 312 of the shaft 310. The wire 314 is shown to extend throughout the handling and manipulation shaft HMA, entering through the catheter actuator 302, and exiting through the catheter distal portion 306. The wire 314 is configured to freely translate throughout the shaft lumen 312. The wire distal end 314-D may have a nose tip 316 with a smooth rounded and convex distal surface configured for ease of insertion into a conduit BV. The embodiment 300 may be made of stainless steel for example, or of other materials known to those skilled in the art.

Figure 29:
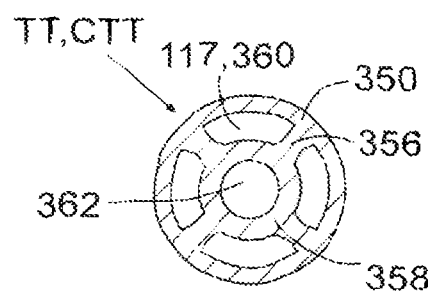

A tube tool TT, such as a catheter tube tool CTT for example, may be disposed in the catheter lumen 352 at the distal end portion 350-D of the catheter 350. A cross-section A-A cut in FIG. 28 through the distal portion 350-D supporting the tube tool TT, or catheter tube tool CTT, is shown in FIG. 29. The catheter tube tool TT or CTT, may be supported distally in the lumen 352 of the catheter 350 by a plurality of radially extending legs 356 that support a central sleeve 358, which sleeve may be concentric with the catheter. A plurality of tube tool thread ducts 117, or tube tool openings 360, may be disposed intermediate between the plurality of legs 356 to provide passage from the proximal side CTT-P to the distal side CTT-D of the tube tool CTT. In other words, the tube tool TT or CTT may include a plurality of tube tool thread ducts 117, or tube tool duct openings 360 that may be disposed intermediate between the catheter 350 and the central sleeve 358 to form the legs 356 therebetween. The tube tool CTT may have a selected number of tube tool duct openings 360, which openings may have a shape chosen according to practical needs, such as for example the circular shape of a bore, which example is not shown in FIG. 29. The duct openings 360 shown in FIG. 28 may be disposed at an angle β relative to the axis X of the stranded tube ST, however, the angle β is not shown in FIGS. 28 to 30.

The central sleeve 358 is configured to operate in association with the tube tool duct openings 360 to unwind wound threads 102 for passage thereof from the proximal portion TT-P to the distal portion TT-D of the tube tool TT as unwound threads 105. The sleeve 358 may have a central sleeve passage 362 sufficiently large to permit free translation therethrough of the wire 314.

In FIGS. 28 and 29, the central sleeve 358 is shown to have a cross-section profile resembling the profile of a wing, where the leading edge 364 may be oriented toward the distal direction DST and the trailing edge 366 may point to the proximal direction PRX. The legs 356 are attached to the catheter 350 and to the extrados 368 of the central sleeve 358. Such a configuration of the tube tool CTT allows the tube tool openings 360 not only to unwind wound threads 102, but also to rewind unwound threads 105 back into a tightly wound stranded tube ST. Rotation of the stranded tube ST contrary to the winding direction of the stranded tube will rewind the liberated unwound threads 105 and rebuild the stranded tube back into a tightly wound structure. Thereby, the tube tool CTT is operable for unwinding the wound and coiled threads 102 and for rewinding of the unwound coiled threads 105.

In FIG. 28, the actuator 302 is used to operate the stranded tube ST for anchoring of and into the corpus COR, for example, for proximal retrieval thereof out of a conduit BV. The catheter actuator 302 has a shaft handle 330 and a catheter handle 332. The shaft handle 330 is fixedly coupled to the proximal portion 310-P of the shaft 310, and the catheter handle 332 is fixedly coupled to the proximal portion 350-P of the catheter 350. The shaft handle 330 has a shaft handle adaptor 334 which is disposed in longitudinal extension therewith, and a male screw thread 336. The shaft handle 330 is proximal to the shaft handle adaptor 334 that is proximal to the male screw thread 336. The male screw thread 336 is configured for screwable engagement with a matching female screw thread 338 disposed in and pertaining to the catheter handle 332. The catheter handle 332 is configured to allow free rotation therein and thereout of the male screw thread 336. Hence, the male screw thread 336 is free to rotate in both clockwise and anti-clockwise directions. Likewise, the male screw thread 336 is configured to allow free rotation over of the female screw thread 338 in both clockwise and anti-clockwise directions. Therefore, the male screw thread 336 and the female screw thread 338 are free to rotate in both clockwise and anti-clockwise directions. Moreover, the actuator 302 is configured to provide unhindered distal and proximal freedom of displacement for free relative rotation of the male screw thread 336 and of the female screw thread 338. The catheter 350 may be retrieved proximally out of the conduit BV while the wire 314 remains in place therein. This permits replacement of the catheter 350 by another tool or device, which may be guided distally into the conduit BV over the wire 314.

The shaft handle adaptor 334 may be marked with a scale of graduations for the same purposes as described with respect to the embodiment 200, although not shown as such in FIG. 28. Likewise, the embodiment 300 may be equipped with radiopaque marker(s) or be made of material featuring radiopacity, as described with respect to the embodiment 200. Furthermore, a shaft stopper 242 may be disposed on the shaft handle adaptor 334, as with the embodiment 200 described hereinabove and shown in FIG. 25.

For the anchoring of and into a corpus COR, the stranded tube ST has to be engaged with the corpus and then unwound to liberate at least one, or a plurality, or the entirety of wound coiled thread(s) 102. Unwinding of the stranded tube ST liberates at least one, or a portion, or the plurality of the tightly prestressed helicoidally coiled and wound thread(s) 102. The wound threads 102 then separate and extend away from the stranded tube ST, possibly in radial direction, into unwound threads 105, similar to the unwinding shown in FIG. 10.

In FIG. 28, the distal portion ST-D of the stranded tube ST is shown supported by the trailing edge 366 of the catheter tube tool CTT. Unwinding of the distal portion ST-D is achieved by pushing the stranded tube ST, distal portion ST-D first, over the trailing edge 366, and then, while still pushing distally, in winding direction rotation through the tube tool thread ducts 117, or tube tool openings 360 of the catheter tube tool CTT.

The tube tool openings 360 of the catheter tube tool CTT may be configured to unwind wound and coiled threads 102 and to rewind unwound coiled threads 105 back into wound coiled threads. Furthermore, each unwound helically coiled thread 102 has a distal thread extremity 108, and at least one such distal thread extremity may be disposed to protrude to the distal side CTT-D of the catheter tube tool CTT and out of a tube tool openings 360 prior to engagement with the corpus COR. Optionally, the at least one thread extremity 108 may have a distal thread retention means 108F, which is configured to prevent proximal retrieval of the unwound thread(s) 105 to the proximal side CTT-P and out of the tube tool opening 360. One distal thread retention means 108F suffices to prevent proximal retrieval of a plurality of unwound threads 105 out of the tube tool conduits 117, or tube tool duct openings 360. Distal thread retention means 108F are shown in FIG. 11.

Figure 30:
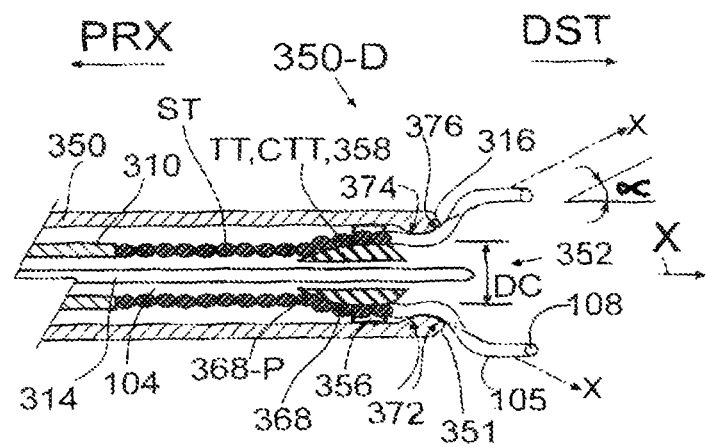

FIG. 30 illustrates a stranded tube ST pushed distally and rotated to unwind by being forced through the tool tube thread ducts 117, or tool tube openings 360, shown in FIG. 29, of the catheter tube tool CTT. Only two wound threads 102 are shown in FIG. 30 for the sake of clarity. As shown, the wound threads 102 have been unwound and liberated to extend distally and possibly radially as unwound threads 105. Radial divergence of the unwound threads 105 may be controlled, as described hereinbelow.

Reference is made to FIGS. 28 to 30 regarding the operation and use of the actuator 302 to unwind the wound threads 102.

Handling and manipulation shafts HMA, well known to those skilled in the art, may be configured to support both the stranded tube ST and the tube tool TT or CTT. The term engagement herein means disposition of the stranded tube ST in operative relation with the corpus COR. Once the stranded tube ST is navigated to and engaged as desired, an operator, not shown, may firmly hold the catheter handle 332 stationary with one hand while rotating the shaft handle 330 with the other hand. Rotation of the shaft handle 330 will rotate the male screw thread 336 over the stationary female screw thread 338 and forcefully push the tube distal portion end ST-D over the extrados 368 of the catheter tube tool CTT. By being forced through the tube tool openings 360, the tube distal portion end ST-D of the stranded tube ST will unwind and the tightly wound threads strand 102 will be liberated to expand distally and possibly radially. Unwinding of the wound threads 102 is obtained by rotation of the shaft handle 330 in a same direction of rotation as the winding direction of the stranded tube ST. The winding direction of the stranded tube ST is the same as the thread windings of both the male screw thread 336 and the matching female screw thread 338. If desired, as described hereinabove with respect to the embodiment 200, shaft handle graduations may be marked on the shaft handle adaptor 334 and radiopaque materials or radiopaque markers means may also be added.

With the configuration of the catheter tube tool CTT, distally liberated unwound threads 105 may be stranded back, or re-stranded, into wound threads 102 to form and rebuild an original tightly coiled stranded tube ST. Hence, unwound threads 105 may regain their original shape and return to form a wound stranded tube ST. Evidently, the direction of rotation for stranding back unwound threads 105 into a stranded tube ST is opposite to the direction of rotation for unwinding the stranded tube. This means that the tube tool CTT has tube tool openings 360 configured to unwind wound coiled threads and to rewind unwound coiled threads back into wound coiled threads.

The angle α of radial expansion of the unwound and liberated threads 105 may be controlled and commanded by parameters including the pitch 103 of the stranded tube ST, the shape of the catheter tube tool CTT, and the configuration of the structure of the catheter distal portion 350-D. The catheter tube tool CTT operates in association with the catheter distal portion 350-D for the control of the angle α.

FIG. 30 illustrates the unwinding of wound threads 102 relative to the catheter distal portion 350-D and to the wire 314. If desired, the wire 314 may be used initially as a guiding rail configured to navigate the catheter 350 for engagement with the corpus COR and may be translated distally out of the distal portion 350-D to participate in the anchoring of and into the corpus COR. Else, the wire 314 may be retrieved proximally into the catheter 350, or may be disposed in an intermediate position, about flush with the catheter nose 351, as shown in FIG. 30, or be completely retrieved proximally out of the catheter 350. Alternatively, the wire 314 may be used as a guiding rail configured for guiding tools and implements thereover to the corpus COR, after proximal retrieval of the hollow shaft 310 out of the catheter 350.

The catheter nose 351 of the catheter distal portion 350-D may have one or more radial expansion angle control surfaces 372, which may be configured and appropriately oriented to dictate the magnitude of the angle α. For example, a converging surface 374 and a diverging surface 376 may be disposed distally of the catheter tube tool CTT in the catheter lumen 352. The converging surface 374 may be shaped to constrain the angle α, to allow control of the convergence of unwound threads 105. Likewise, the diverging surface 376 may permit control of the divergence of unwound threads 105.

Control of the angle α of expansion of unwound threads 105 may also be effected by the configuration of the extrados 368 of the catheter tube tool CTT, by the slope of the proximal portion 368-P of the extrados 368, and by the exterior diameter DC of the central sleeve 358. Both the extrados 368 and the converging surface 374 may operate in association to control the expansion and the angular convergence of unwound distally extending threads 105.

Likewise, the extrados 368 and the diverging surface 376 may be configured to control an increase of the angle α, to allow radial expansion of the unwound threads 105 if desired. There are thus available a plurality of parameters and mechanisms operative alone or in combination for the control of the angle α of radial expansion, expansion in parallel to the wire 314, radial convergence, as well as the distal extension of unwound helically coiled threads 105.

Hence, parameters commanding the angle α of radial expansion of the unwound thread 105 may include the pitch distance 103, the material from which the stranded tube ST is made, the mechanical properties of the stranded tube ST such as dimensions and pre-stress of the threads 102, the shape of the tube tool TT, the configuration and the duct angle β of the tube tool thread ducts 117 or 360, alone and/or in association with the configuration of the catheter distal portion 350-D, as described hereinbelow, and the exterior diameterΔ of the tube tool, which is shown in FIG. 4.

The embodiments described hereinabove and hereinbelow may be made out of materials, and may be manufactured, by techniques well known to those skilled in the art. The stranded tube ST may be acquired according to specification of material and of surface treatment. For example, the stranded tube ST and the various embodiments of the tube tool TT may be coated with a product 380, not shown in the Figs., such as a friction-reducing coat or layer of solid lubricant that may enhance smooth operation, such as Teflon for example, which is a registered Trademark. Both the stranded tube ST and the tube tool TT may be made out of metal, plastic material, natural material, or synthetic material, our out a combination of materials, and may include radiopaque material and/or may carry radiopaque markers.

Additional Exemplary Embodiments

The stranded tube ST was described hereinabove as a tubular bundle of tightly wound threads 102 operable with a tube tool TT for liberation from a wound state WND to an unwound state UNW. One use of the stranded tube ST is the liberation of unwound threads 105 for the anchoring of and into a corpus COR disposed distally away in a conduit BV, after navigation thereto and engagement therewith. Next, it is possible to proximally retrieve the anchored corpus COR by proximal retrieval of the stranded tube ST.

Unwound threads 105 used for the anchoring of and into a corpus COR may permit the concurrent anchoring of more than one corpus, and may thereby provide a fastener operable for a lengthy period of time, such as days, weeks, months, and even years. One may thus operate even at least one anchored unwound thread 105 as a fastener 130. For practical purpose however, such a use may require to retrieve the tube tool TT and the handling and manipulation shaft HMA, but not the stranded tube ST operative as a fastener, out of the conduit BV.

Another use of such a fastener having threads 102 that are coated with a product 380, not shown in the Figs., which product is operative for affecting the corpus COR, is also possible. For example, one may consider threads 102 coated with a chemical product 380 operative for the dissolution of a plug blocking the flow of a fluid in a conduit BV. Evidently, it would be advantageous to retain the unwound threads 105 in the plug until dissolution thereof and reestablishment of fluid flow, without having to keep the tube tool TT or CTT and the handling and manipulation shaft HMA in the conduit BV.

With the embodiments described hereinabove, a stranded tube ST operative as a fastener simply requires the disconnection of a relatively short length of stranded tube from the supporting handling and manipulation shaft HMA, as described hereinbelow.

Figure 31:
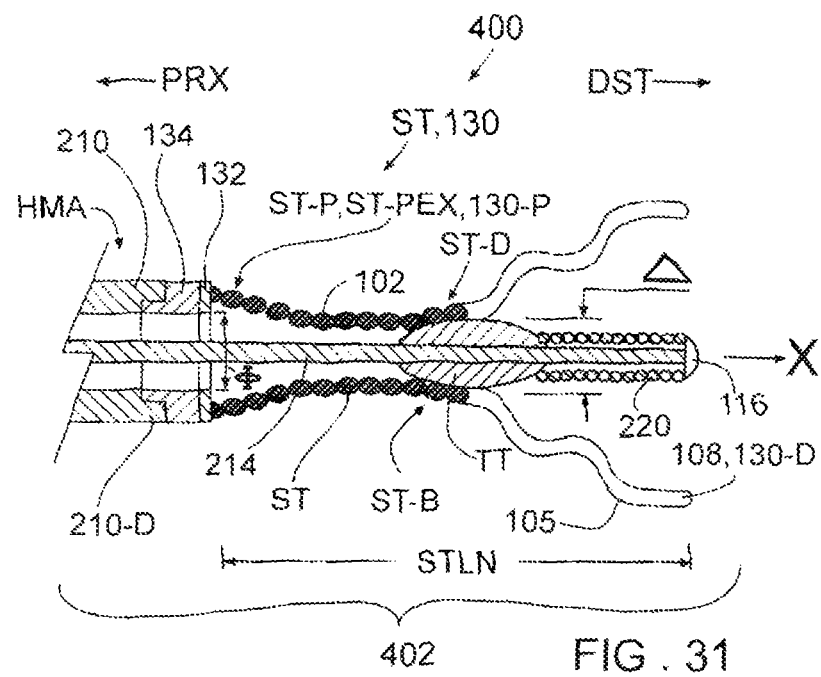
FIGS. 31 and 31A show an embodiment for use as a fastener.

FIG. 31 shows an exemplary embodiment 400 depicting a stranded tube ST for use as a fastener 130. The embodiment 400 is supported by a handling and manipulation shaft HMA similar to the one described with reference to the embodiment 200 shown in FIGS. 25 to 27. In FIG. 31, the distal portion 402 of the embodiment 400 shows a modification of the distal portion 210-D, which modification may be applied to the navigation intermediate portion 204 and to the actuator 206 of the embodiment 200. The wire 214, the tube tool TT, the nose tip 216, and the helicoidal guidance spring 220 may be the same and operate in the same manner as described with respect to the embodiment 200.

The handling and manipulation shaft HMA, not shown in FIG. 31, may have a hollow shaft 210 wherethrough passes a wire 214 fixedly supporting a tube tool TT. The distal portion end 210-D of the shaft 210 supports a length of stranded tube ST which is an operative portion of a fastener 130. In FIG. 31 the distal portion ST-D of the stranded tube ST, which is the distal portion of the fastener 130, is partially unwound and the proximal portion end ST-P of the stranded tube is slightly flared to form a proximal flared extremity ST-PEX. Only two unwound threads 105 are shown in FIG. 31 for the sake of clarity.

The stranded tube ST may be easily flared in elastic or plastic deformation by use of a jig or any other appropriate tool, or be ordered as a factory flared stranded tube 130. The driven ring 132 is fixedly coupled to the proximal flared extremity ST-PEX, which is the proximal portion end ST-P of the stranded tube ST. The driven ring 132 may be glued or welded to the proximal flared extremity ST-PEX, such as by laser welding for example or by other techniques well known to those skilled in the art. The body ST-B of the stranded tube ST, ranging distally away from the proximal flared extremity ST-PEX may be cylindrical, frusto-conical, or convergent-divergent and end as a distal portion end ST-D of the stranded tube.

Contrary to the embodiment 200, the stranded tube ST, and thus the fastener 130, is releasable and detachable from the shaft 210. Furthermore, the length STLN of the fastener 130, or stranded tube ST is selected as desired, from a few centimeters to one millimeter.

There is provided a shaft driver 134 which in the proximal direction PRX is fixedly coupled to the distal portion 210-D of the shaft, and which in the distal direction DST, detachably supports the driven ring 132. The shaft driver 134 is configured for rotation of the driven ring 132, which is fixedly coupled to the proximal flared extremity ST-PEX of the stranded tube ST.

Figure 32:
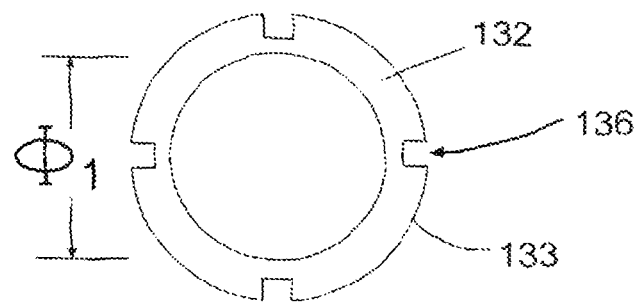
FIGS. 32 and 33 illustrate elements of the embodiment shown in FIG. 31, FIGS. 34 to 38 depict various anchoring configurations of a fastener.
Figure 33:
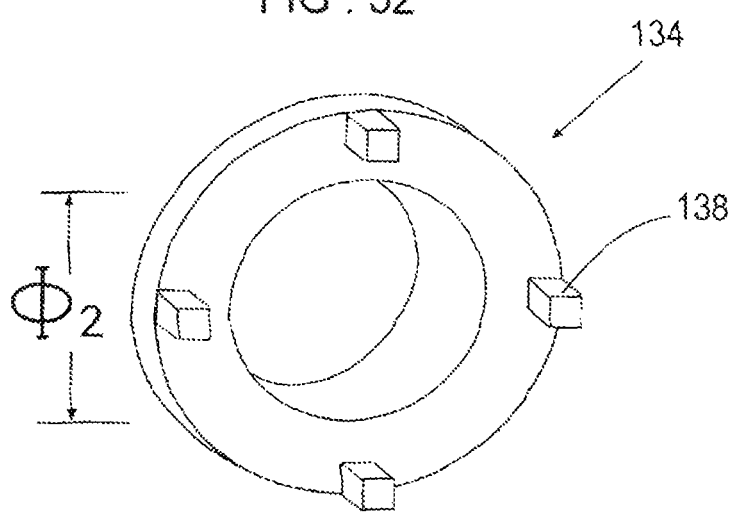

Reference is made to FIG. 32 showing a driven ring 132 and to FIG. 33 illustrating a shaft driver 134. FIGS. 32 and 33 are an example of a coupling mechanism permitting the release of the stranded tube ST from the shaft 210. Many other coupling mechanisms may provide the same results. Furthermore, the tube tool TT may be configured as desired according to the descriptions hereinabove related to the embodiments illustrated with respect to FIGS. 4 to 7.

FIG. 32 is a top elevation of an exemplary driven ring 132 having an interior ring diameter Φ1. The interior ring diameter Φ1 of the flared extremity ST-PEX may be just as small as the interior diameter d of the stranded tube ST, shown in FIG. 1, plus twice the diameter of a thread 102. However, the interior diameter of the shaft 210, of the driven ring 132 and of the proximal flared extremity ST-PEX have to be larger than the exterior diameter Δ of the tube tool TT.

The driven ring 132 may carry a portion of the coupling mechanism permitting rotational motion and release of the stranded tube ST from the shaft 210. For this purpose, the driven ring 132 may have a ring periphery 133 supporting for example at least two fastener slots 136. Four such fastener slots 136 are shown in FIG. 32.

FIG. 33 is an isometric representation of an exemplary shaft driver 134 configured to match the driven ring 132. The shaft driver 134 should have an interior driver diameter Φ2 equal at least to the exterior diameter Δ of the tube tool TT. Driver protrusions 138 of desired number, shape, and dimensions configured to match the fastener slots 136 may be distributed on the driver periphery 135 of the shaft driver 134. FIG. 33 shows four such driver protrusions 138 in a distribution matching the four fastener slots 136 shown in FIG. 32.

Reference is made again to FIG. 31. With the driver protrusions 138 inserted into the fastener slots 136, while the wire 214 is kept stationary, the distal portion 210-D of shaft 210 may be pushed distally to apply force via the shaft driver 134 and the driven ring 132 such that the stranded tube ST will be forced onto the tube tool TT. Rotation of the shaft 210 in the winding direction of the stranded tube ST will rotate the shaft driver 134, which in turn will rotate the driven ring 132 and cause the tube tool TT to unwind the wound threads 102 of the fastener 130. With appropriate engagement of the embodiment 400 with the corpus COR, unwinding of the fastener 130 will releases at least one, a plurality, or the entirety of the unwound coiled threads 105. As described hereinabove, the unwound coiled thread(s) 105 will be liberated for anchoring of and into at least one corpus COR.

To anchor the stranded tube ST of the embodiment 400 as a fastener 130 into at least one corpus COR disposed distally in a conduit BV, an operator, not shown, may first navigate the distal portion 210-D of shaft 210 for engagement with the corpus.

Handling and manipulation shafts HMA configured to support both the stranded tube ST and the tube tool TT are well known to those skilled in the art, and are similar to guide wire shafts, catheter shafts, and guiding catheter shafts for example.

The term engagement here signifies selected disposition of the stranded tube ST operative as a fastener 130, in operable relation with the corpus COR. This means that the stranded tube ST is disposed into, or in abutment with, or adjacent proximally to the penetrable corpus COR.

The distal end portion ST-D of the fastener 130 is now unwound to liberate at least one wound thread(s) 102 distally as at least one unwound thread(s) 105 configured for the anchoring of and into the at least one corpus COR. The unwound thread(s) 105 may fan-out into the at least one corpus COR as a web of spread out unwound threads 105 for firm anchoring of and into the corpus which is held in strong retention. Thereafter, the shaft 210, the wire 214, the nose tip 216, and the helicoidal guidance spring 220 may be retrieved proximally together with the tube tool TT, leaving the stranded tube ST anchored as fastener 130 in at least one corpus COR.

The driven ring 132 of the released fastener 130 thus has as a proximal end 130-P, while the distal end(s) 108 of the unwound thread(s) 105 form(s) the distal portion end of the fastener.

Figure 31A:
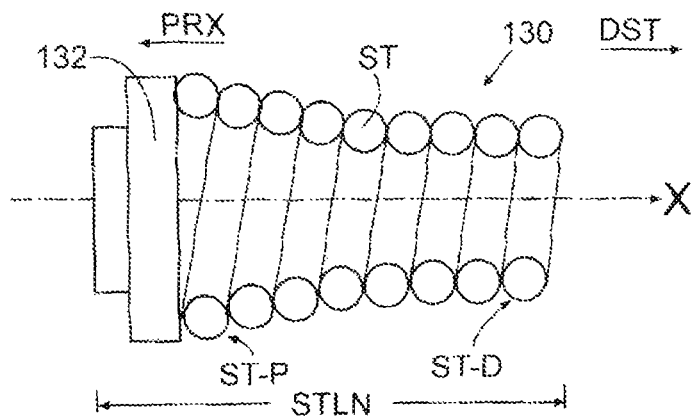

FIG. 31A shows an exemplary side elevation of an unwound fastener 130 having a length STLN. The fastener 130 includes a stranded tube ST which is fixedly coupled to a driven ring 132. The stranded tube ST and the driven ring 132 may be longitudinally aligned along the axis X.

As described hereinabove, the shaft driver 134 is configured for releasable disconnection from the driven ring 132 by proximal translation away therefrom. The tube tool TT will be retrieved proximally through the interior ring diameters Φ1 of the driven ring 132 and the interior driven diameter Φ2 of the shaft driver 134, which are larger than the exterior diameter Δ of the tube tool TT. Hence, the tube tool TT may be retrieved proximally out and away through the interior diameters of the proximal flared extremity ST-PEX of the stranded tube ST, of the driven ring 132, of the shaft driver 134, and of the shaft 210, where those interior diameters are all larger than the exterior diameter Δ of the tube tool TT. It is understood that if necessary, the tube tool is able to expand the interior diameter d of the stranded tube ST to the exterior diameter Δ of the tube tool TT to pass therethrough. After the wire 214 holding the tube tool TT, the nose tip 216, and the helicoidal guidance spring 220 have been retrieved proximally away, the shaft 210 may remain in place, for example, as a guide for the introduction therethrough of tools and/or products 380 for use with the corpus COR and/or with the conduit BV. Alternatively, the shaft 210 may be retrieved proximally away, leaving the wire 214 in place as a guide for the introduction thereover of tools and/or products 380 for use with the corpus COR and/or with the conduit BV.

An unwound stranded tube ST may thus be operable as a self-threading and self-retaining fastener 130 for anchoring of and into one or more corpora COR, and may be operable for the joining together of penetrable corpora COR and/or with penetrable physical objects. The anchoring with one or more fasteners 130 may be used for the fastening together of corpora COR, and/or for the retention in selected disposition and orientation of devices, medical implements, or implants, such as aortic or other stent grafts for example.

Anchoring of one or more fastener(s) 130 having wound threads 102, and thus unwound threads 105 coated with a product 380 may be beneficial at least for example, for providing products, such as medication and/or preparations for example, to at least one corpus COR. Furthermore, one or more fasteners 130 may be advantageous to attach together or retain in place of at least one device or implement.

In FIGS. 34 to 38, one fastener 130 and two unwound threads 105 are shown schematically for the sake of clarity. However, the number of fasteners 130 is not limited to one fastener, and the number of unwound threads 105 is not limited to one or two. The length STLN of the stranded tube ST operative as a fastener 130 may be selected according to needs or desire.

FIGS. 34 to 38 schematically illustrate various examples of fixed dispositions of a stranded tube ST operative as a fastener 130 and configured for the anchoring of and into at least one corpus COR. Only two unwound threads 105 are shown for the sake of clarity.

Figures 34, 35, 36:
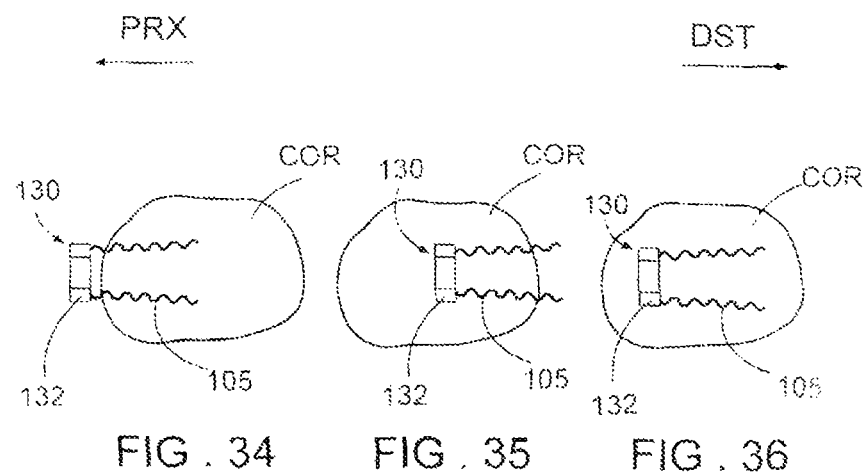

FIG. 34 presents an example of a fastener 130 where the unwound threads 105 liberated out of a wound and stranded tube ST are operative as a fastener 130. The unwound threads 105 extend from proximally to the corpus COR to the interior thereof, and are anchored partially into a proximal portion of a corpus. However, although not shown in FIG. 34, the unwound threads 105 may protrude distally out and away from the corpus COR.

FIG. 35 depicts an example a fastener 130 anchored in the interior of a corpus COR, with a distal portion of the unwound threads 105 extending distally out of the corpus. With FIG. 36, the unwound threads 105 of the fastener 130 are anchored in the interior of a corpus COR but do not protrude thereout.

Figures 37, 38:
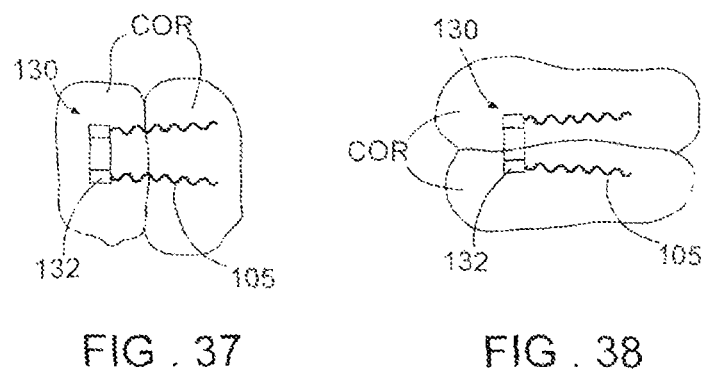

FIG. 37 illustrates an example of the use of a fastener 130 for the anchoring of and into two corpora disposed in proximal to distal longitudinal succession. The unwound threads 105 of the fastener 130 are shown embedded in the interior of both corpora COR but may extend proximally and/or distally thereout although that case is not depicted as such in FIG. 37.

FIG. 38 illustrates two corpora COR anchored side by side, each one by different unwound threads 105. A fastener 130 may anchor at least one, thus more than two corpora COR. The unwound threads 105 of the fastener 130 are shown embedded in the interior of both corpora COR but may extend proximally and/or distally thereout although that case is not depicted as such in FIG. 38.

Figure 39:
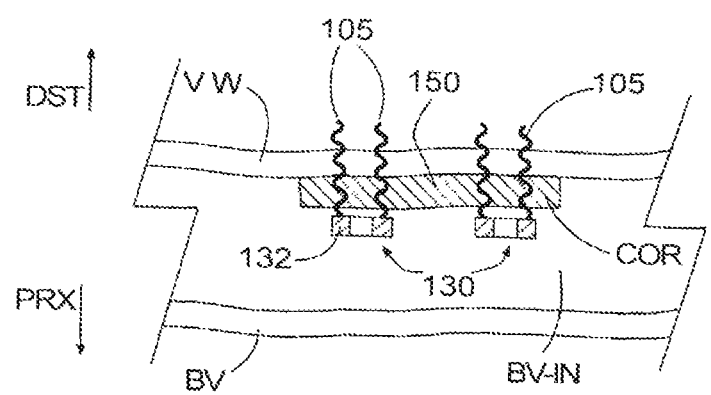
FIGS. 39 and 40 illustrate fastening in a conduit.
Figure 40:
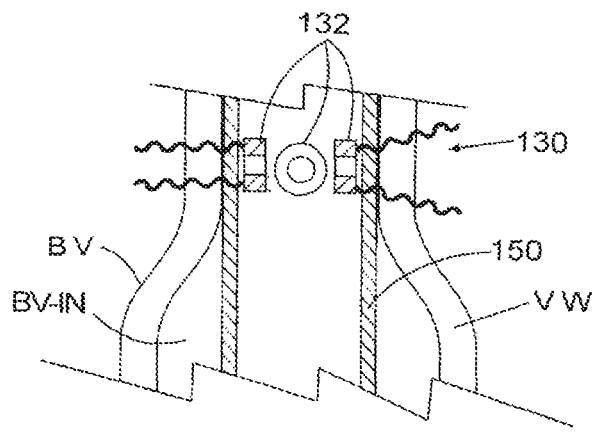

FIGS. 39 and 40 schematically show a fastener 130 for the retention of an implement 150 to a corpus COR and/or to a conduit BV, such as a blood vessel or a conduit of the anatomy. The insertion of a fastener 130 may take advantage of a handling and manipulation shaft HMA such as a pre-shaped guiding catheter, not shown in the Figs. A pre-shaped guiding catheter is operable for engagement of a conduit BV perpendicular to a conduit wall VW.

FIG. 39 is a cross-section of a conduit BV showing the use of stranded tubes ST operable as fasteners 130. Fasteners 130 may be disposed in the interior BVIN of a conduit BV, and anchor the penetrable implement 150, such as a stent graft for example, to a conduit wall VW. The unwound threads 105 anchor both the implement 150 and the vessel walls VW of the conduit BV. Thus one fastener 130 may anchor into at least one corpus COR and at least one implement 150, and may anchor into a corpus COR, and/or a conduit BV, and/or an implement 150, in desired combination. The unwound threads 105 may be restricted to extend in the interior of both the penetrable implement 150 and the conduit BV, or may extend proximally thereout and/or distally. Escape of fluid out of the vessel walls VW is prevented by the elasticity of the vessel walls VW of the conduits BV and thanks to the minute diameter of the unwound threads 105. Else, a sealing product 380 coated on the threads 102 may stop a leak. Thus, at least one coiled thread of the fastener 130 may be coated with a product 380, and the product may be operative to affect the corpus COR, and/or the conduit BV. If desired, more than one fastener 130 may anchor the implement 150, as shown in FIG. 39.

FIG. 40 is a cross-section of a conduit BV showing the use of a stranded tube ST operable as a fastener 130 for the anchoring of and into more than one corpus COR. A fastener 130 is shown anchoring two corpora COR, where the second corpus may be a penetrable body or a penetrable implement, such as a penetrable graft stent 150 for example. In FIG. 40, three fasteners 130 are seen to operate for the directional anchoring in oriented disposition of and into the second corpus 150 disposed distally in a conduit BV, such as an abnormally dilated blood vessel for example. The unwound threads 105 of the fasteners 130 are shown substantially perpendicular to the conduit BV but other configurations are evidently possible. The number of fasteners 130 and the length STLN of the stranded tubes ST may be selected as desired or according to needs.

A body is accepted as being penetrable when unwound threads 105 are capable of passing therethrough, even if the material wherefrom the body is made is impenetrable. For example, a wire mesh made of steel is penetrable since the unwound threads 105 are able to pass through the meshes which are interstices between the steel wires. Hence, an electrical wire may also be considered as a penetrable body since the unwound threads 105 may pass around the wire for anchoring thereof with and into another corpus COR. The same is true for a body packaged in a penetrable material: the fastener 130 may anchor the portion of penetrable material holding the packaged body.

A stranded tube ST operable as fastener 130 may also be considered as an electrode 130 or as an electrical lead, when the threads 102 are acceptable as being conductors of electricity. An electrode 130 may be coupled in electrical communication with at least one electrical lead of electricity or with an electrical device. For example, unwound threads 105 of the implement 150 shown in FIG. 39 may operate as electrodes or electrical leads. The driven ring 132 of the fastener 130 may be made out of electrically conductive material or be configured as an electrical device, or support an electrical or a mechanical device. In addition, the driven ring 132 may be configured as a support for a medical device, or a medical implement 150. An electrical device or medical implement may be selected for example, as a medication-releasing device, a signal returning device, a measuring device, or another device for medical use. In other words, a fastener 130 may have at least one unwound thread 105 that is operable as an electrode and/or as an electrical lead that conducts electricity or electrical signals, and the driven ring 132 may be operable as an electrical device 150, and/or may support an electrical device 150, a mechanical device, or another operable device 150. A fastener 130 may also be made of dielectric material.

A fastener 130 may include visual indicators and/or radiopaque markers, and/or be made out of radiopaque material to indicate the disposition and the orientation of the unwound threads 105 and/or of the driven ring 132 to an operator, not shown in the Figs.

Even though anchoring may be easily understood, the unwinding of the prestressed wound and coiled threads 102 of the stranded tube ST into rotating unwinding threads 105 is less intuitive. To help therewith. FIGS. 41 to 44 present photographs taken under a microscope at an enlargement of times 40, illustrating steps of the unwinding process.

Figure 41:
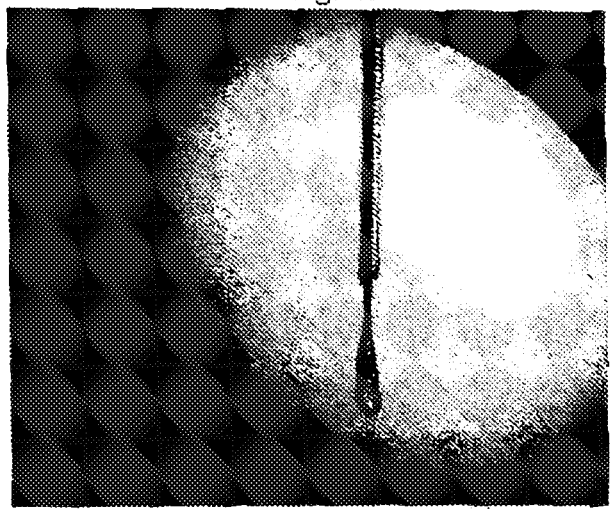

FIG. 41 shows the stranded tube ST, the wire 110, and the tube tool TT. The wire 110 exits out of the stranded tube lumen 104 at the distal portion end ST-D of the plurality of prestressed and tightly unwound threads 102. The distal end of the wire 110 supports the tube tool TT.

Figure 42:
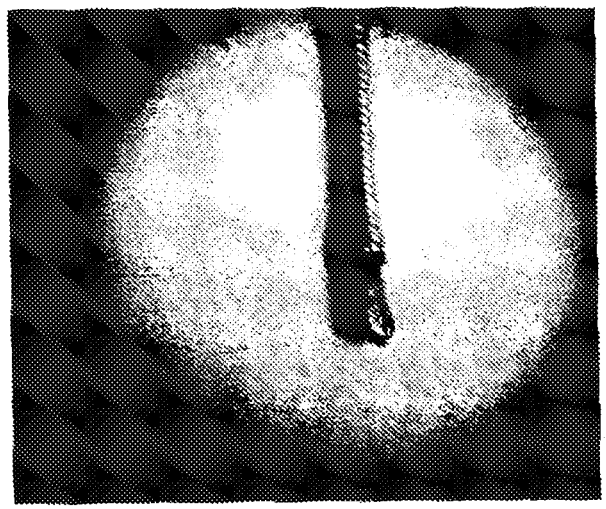

In FIG. 42, the stranded tube ST has been advanced into distal engagement over the wire 110 for the distal portion end ST-D to abut to the tube tool TT. Pushing of the stranded tube ST onto the tube tool TT and rotation of the stranded tube ST will start the unwinding process.

In FIG. 43, the unwinding process has just begun. The stranded tube ST has been pushed and rotated over the tube tool TT. The unwinding process has unwound the wound threads into distally fanned-out unwound threads 105. Further distal pushing onto and in relative rotation over the tube tool TT, shown in FIG. 44, will liberate an additional length of distally unwound threads 105 in fanned-out extension. Unfortunately, only a video clip is able to visually present the rotational unwinding and "corkscrewing" of the threads 105 while unwinding.

The embodiments described hereinabove may be made from common materials well known to those skilled in the art, such as stainless steel, or plastic materials for example, and do not require expensive materials such as Nitinol.

In the embodiments described hereinabove, the stranded tube ST has a first not deployed and wound state WND, and a second deployed and unwound state UNW. The stranded tube ST is acquired in the wound state WND, and in operation, is navigated for engagement with the corpus COR in the same wound state. One distinguishing feature of the embodiments described hereinabove is that external forces are not applied on the stranded tube ST when in the wound state WND, such as during distal or proximal navigation through a conduit BV. In contrast therewith, external force is applied onto stranded tube ST for the unwinding thereof out of the first not deployed and wound state WND, towards the second deployed and unwound state UNW. Once the unwinding of stranded tube ST has stopped there is no external forces that is applied thereto, unless for rewinding back towards the wound state WND of the stranded tube.

It is understood that when the distal end of unwound threads 108 are disposed in the thread ducts 117, 118, 119 or 360, there is no application of external force on the stranded tube ST. The same is true when the distal end of an unwound thread 108 is crimped into a thread retention or flat end 108F. An external force is operated on the stranded tube ST for unwinding or for rewinding and is accepted as a force that is applied by or via the handling and manipulation shaft HMA, or by the tube tool TT or catheter tube tool CTT. Contrary to the background art, the embodiments described hereinabove do not require the operation of restraining elements to apply external force on an intervention device or tool during navigation through a conduit BV.

There is thus described a method for engaging the stranded tube ST which includes navigating the stranded tube to the corpus COR while the stranded tube is disposed in the wound state WND and is free from application thereon of external force. Likewise, there is described a system wherein the stranded tube ST is navigated toward the corpus COR in the wound state WND and is free from operation thereon of external force applied by at least one of the handling and manipulation shaft HMA, and the tube tool TT or catheter tube tool CTT. External force is not applied to the stranded tube ST during distal or proximal navigation though a conduit BV, both before and after anchoring the corpus COR while being disposed in either one of the wound or unwound state, respectively WND and UNW.

It will be appreciated by persons skilled in the art, that the present invention is not limited to what has been particularly shown and described hereinabove. Rather, the scope of the present invention is defined by the appended claims and includes both combinations and subcombinations of the various features described hereinabove as well as variations and modifications thereof which would occur to persons skilled in the art upon reading the foregoing description. The various embodiments described hereinabove may be taken alone and in combination to form embodiments that are not described, such as including materials, mountings, assemblies, couplings, and attachments of elements selected according to practice well known to those skilled in the art. Furthermore, the stranded tube ST may be made of strands from made from the same material, or from different materials, or from hybrid materials, or from composite materials.

INDUSTRIAL APPLICABILITY

The embodiments described hereinabove are applicable for production by industry, and in particular by industries dealing with medical shafts.

REFERENCE SIGNS LIST

BV blood vessel conduit
BVIN interior of conduit
COR corpus
COR-D distal portion end of COR
COR-EX exterior of the penetrable corpus
COR-IN interior of the corpus
COR-P proximal portion end of COR
CTT catheter tube tool
CTT-D distal side of catheter tube tool CTT
CTT-P proximal side of catheter tube tool CTT
D exterior diameter of the ST
DC exterior diameter of CTIT
DST distal direction
HMA handling and manipulation shaft, device, or system
PRX proximal
R direction of rotation
ST stranded tube
ST-B body of the stranded tube ST
ST-D distal portion end of the ST
STLN length of the stranded tube ST
ST-P proximal portion end of the ST
ST-PEX stranded tube proximal extremity
TT tube tool
TT-D tube tool distal portion
TT-EX
TT-P tube tool proximal portion
UNW unwound state
VW conduit wall
WND wound state
x longitudinal axis of unwound thread
X longitudinal axis of the ST
α angle of radial expansion
β duct angle
Δ exterior diameter of TT
Φ1 interior diameter of the ring
Φ2 interior diameter of the driver
100 embodiment
100-D device distal portion
100-P device proximal portion
102 wound thread 102
103 pitch distance
104 ST lumen
105 unwound thread
108 distal end of unwound thread
108F thread retention, flat end
110 wire
110-D wire distal end
110-P wire proximal end
117 thread duct
118 grove
119 conduits
122 hollow cone frustum
124 rim
130 fastener
130-D fastener distal end
130-IP fastener proximal end
132 driven ring
133 ring periphery
134 shaft driver
135 driver periphery
136 fastener slot
138 driver protrusion
150 implement
200 embodiment
202 navigation distal portion
204 navigation intermediate portion
206 actuator 206
210 shaft
210-D shaft distal portion
210-P shaft proximal portion
212 shaft lumen
212-D shaft lumen distal portion
214 wire
214-D distal wire portion
214-P proximal wire portion 216 nose tip
218 wire distal end
220 guidance spring
230 wire handle
232 shaft handle
234 wire handle adaptor
236 wire handle male screw thread
238 wire handle female screw thread
240 wire handle graduations
242 wire stopper
300 embodiment
302 navigation catheter distal portion
304 navigation catheter intermediate portion
306 catheter actuator
310 shaft
310-D distal portion of the shaft
310-P proximal portion of the shaft
312 shaft lumen
314 wire
314-D wire distal end
314-P wire proximal end
316 nose tip
330 shaft handle
332 sleeve catheter handle
334 shaft handle adaptor
336 male screw thread
338 female screw thread
350 catheter
350-D catheter distal portion
350-P catheter proximal portion
351 catheter nose
352 catheter lumen
352-D distal portion of catheter lumen
356 legs
358 central sleeve
360 tube tool openings
362 central sleeve passage
364 leading edge proximally
366 trailing edge distally
368 extrados
370 intrados
372 angle control surfaces
374 converging surface
376 diverging surface
380 product
400 embodiment
402 distal portion of embodiment 400

The invention claimed is:

1. A method for anchoring a device into at least one corpus disposed in a conduit, the device comprising a stranded tube having a plurality of wound coiled threads, the method comprises:

engaging the stranded tube with the corpus;

unwinding at least one wound thread out of the plurality of wound threads into a helically coiled unwound thread, the unwinding being facilitated by engaging the stranded tube with a tube tool by rotating the stranded tube relative to the tube tool about a longitudinal axis of the stranded tube, such that operating the tube tool causes at least one wound thread to unwind from the tube; and anchoring the at least one unwound thread into the at least one corpus by a rotational corkscrew-like translation and rotation such that rotating and orienting the at least one unwound thread along a respective unwound thread longitudinal axis anchors the at least one unwound thread into the corpus.

2. The method of claim 1, wherein orienting unwound threads comprises positioning the unwound thread longitudinal axis at an angle relative to the longitudinal axis of the stranded tube, and controlling said angle.

3. The method of claim 1, wherein operating the tube tool comprises unwinding wound coiled threads and rewinding unwound threads.

4. The method of claim 1, comprising supporting a distal thread extremity of an unwound thread in at least one thread duct provided in said tube tool.

5. The method of claim 4, further comprising:

disposing at least one distal thread extremity in distal protrusion out of the tube tool thread duct, and providing a thread retention for preventing proximal retrieval of the at least one distal thread extremity out of the tube tool thread duct.

6. The method of claim 1, wherein engaging the stranded tube with the corpus comprises disposing the stranded tube in a position selected from a position proximal to the corpus, a position distal to the corpus, and a position interior to the corpus.

7. The method of claim 1, further comprising a step of retrieving the corpus, after said anchoring.

8. The method of claim 1 wherein during anchoring, a structural reinforcement element of the device is operated to prevent fragmentation of the corpus.

9. The method of claim 1, wherein anchoring further comprises operating an anchored unwound thread as an electrode or an electrical lead.

10. The method of claim 1, further comprising navigating the stranded tube to engagement with the corpus, the stranded tube being navigated in a wound state, free from application of external force thereon.

* * * * *